(12) United States Patent
Vince et al.

(10) Patent No.: US 11,479,579 B2
(45) Date of Patent: Oct. 25, 2022

(54) THERAPEUTIC COMPOUNDS AND METHODS

(71) Applicant: Regents of the University of Minnesota, Minneapolis, MN (US)

(72) Inventors: Robert Vince, Minneapolis, MN (US); Swati Sudhakar More, Minneapolis, MN (US); Abbas Raza, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 112 days.

(21) Appl. No.: 17/256,421

(22) PCT Filed: Jul. 1, 2019

(86) PCT No.: PCT/US2019/040190
§ 371 (c)(1),
(2) Date: Dec. 28, 2020

(87) PCT Pub. No.: WO2020/010021
PCT Pub. Date: Jan. 9, 2020

(65) Prior Publication Data
US 2021/0277055 A1    Sep. 9, 2021

Related U.S. Application Data

(60) Provisional application No. 62/693,312, filed on Jul. 2, 2018.

(51) Int. Cl.
*C07K 5/02* (2006.01)
*A61P 25/28* (2006.01)
*A61K 38/00* (2006.01)

(52) U.S. Cl.
CPC ............ *C07K 5/0215* (2013.01); *A61P 25/28* (2018.01); *A61K 38/00* (2013.01)

(58) Field of Classification Search
CPC ..... C07K 5/0215; C07K 5/0606; A61P 25/28; A61P 25/16; A61K 38/00; A61K 8/46; A61Q 19/08
See application file for complete search history.

(56) References Cited

U.S. PATENT DOCUMENTS

2014/0154192 A1*  6/2014  Vince .................. C07K 5/0215
                                                                    514/17.7

OTHER PUBLICATIONS

More et al [Chemical Research Toxicology, 2017, 30, 777-784] (Year: 2017).*

* cited by examiner

*Primary Examiner* — Sudhakar Katakam
(74) *Attorney, Agent, or Firm* — Viksnins Harris Padys Malen LLP

(57) ABSTRACT

Disclosed herein are compounds of formula I: (I) or pharmaceutically acceptable salts thereof, wherein $R^1$, $R^2$, and $R^3$ may any of the values defined herein, as well as compositions comprising such compounds. Also disclosed are methods for treating diseases including neurodegenerative disorders such as Parkinson's Disease and Alzheimer's Disease.

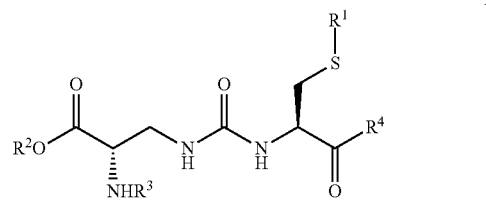

13 Claims, 19 Drawing Sheets

THERAPEUTIC COMPOUNDS AND METHODS

RELATED APPLICATION

This application claims priority to U.S. Provisional Application No. 62/693,312 that was filed on Jul. 2, 2018. The entire content of the application referenced above is hereby incorporated by reference herein.

BACKGROUND OF THE INVENTION

Alzheimer's Disease (AD) is the seventh leading cause of death in the United States. With 5.3 million people currently suffering from the disease, the total expenditure on treatment is as high as 172 billion dollars per year. The AD-afflicted brain shows markedly high indicators of oxidative stress, an umbrella term that describes concentration of species causing oxidative protein, lipid and DNA modification. Examples of such stressors are $Fe^{2+}$, which can abstract an electron from dioxygen to form Reactive Oxygen Species (ROS). Glutathione (GSH) is the primary thiol reductant utilized by physiological pathways that counteract ROS. Unfortunately, GSH administration does not result in significant systemic elevation of GSH levels because of intestinal and hepatic γ-GT.

International Patent Application Publication Number WO2013/009647 discusses certain glutathione analogs of the following formula:

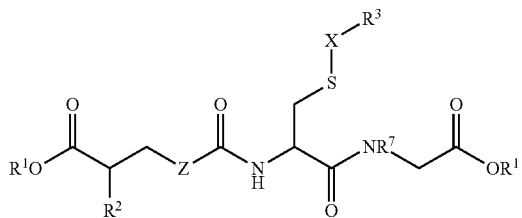

wherein $R^1$, $R^2$, $R^3$, $R^7$, X and Z have the values defined in the application. One compound discussed in WO2013/009647 is p-GSH (pseudo-GSH (ψ-GSH)).

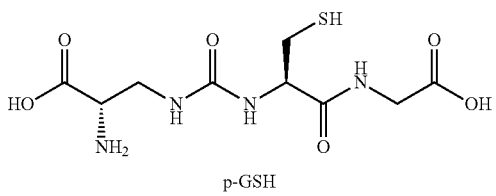 [SMILES: N[C@@H](CNC(=O)N[C@@H](CS)C(=O)NCC(=O)O)C(=O)O]

p-GSH

Certain of the compounds discussed in this publication have unfavorable physical and/or pharmacokinetic properties that may significantly limit their use as pharmaceutical agents. Accordingly, there remains a need for medicinal agents including prodrugs and salts forms thereof to treat diseases such as neurodegenerative disorders (e.g., Alzheimer's Disease) that have improved physical and/or pharmacokinetic properties (e.g., solubility, permeability, stability, or lower presystemic metabolism) and/or improved tissue localization that make them useful as pharmaceutical agents.

SUMMARY OF THE INVENTION

Accordingly, one embodiment provides a compound of I:

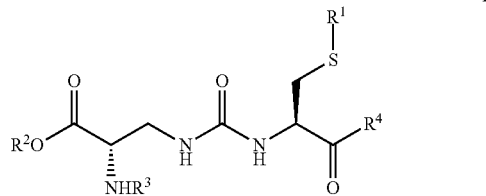

wherein:

$R^1$ is —C(=O)—$R^{1a}$ or —C(=O)O—$R^{1b}$ when $R^4$ is

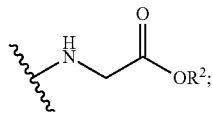

or $R^1$ is H, —C(=O)—$R^{1a}$, or —C(=O)O—$R^{1b}$ when $R^4$ is —$OR^5$;

$R^{1a}$ is ($C_1$-$C_6$)alkyl, ($C_2$-$C_6$)alkenyl, ($C_3$-$C_8$)cycloalkyl, 6-10 membered aryl, 5-10 membered heteroaryl, a residue of formula IIa or IIb:

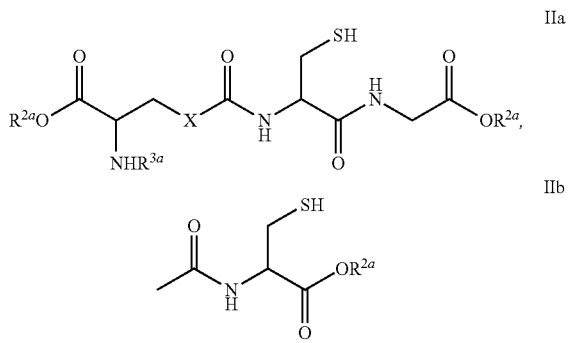

wherein any ($C_1$-$C_6$)alkyl, ($C_2$-$C_6$)alkenyl, ($C_3$-$C_8$) cycloalkyl, 6-10 membered aryl, or 5-10 membered heteroaryl of $R^{1a}$ is optionally substituted with one or more (e.g., 1, 2, 3, 4, or 5) halo, ($C_1$-$C_3$)alkyl, —OH, —SH, or —NHC(=O)($C_1$-$C_3$)alkyl;

X is $CH_2$ or NH;

$R^{1b}$ is ($C_1$-$C_6$)alkyl, ($C_2$-$C_6$)alkenyl, ($C_3$-$C_8$)cycloalkyl, 6-10 membered aryl, or 5-10 membered heteroaryl, wherein any ($C_1$-$C_6$)alkyl, ($C_2$-$C_6$)alkenyl, ($C_3$-$C_8$)cycloalkyl, 6-10 membered aryl, or 5-10 membered heteroaryl of $R^{1b}$ is optionally substituted with one or more (e.g., 1, 2, 3, 4, or 5) halo, ($C_1$-$C_3$)alkyl, —OH, —SH, or —NHC(=O)($C_1$-$C_3$)alkyl;

each $R^2$ is independently H, ($C_1$-$C_6$)alkyl, ($C_2$-$C_6$)alkenyl, ($C_3$-$C_8$)cycloalkyl, 6-10 membered aryl, or 5-10 membered heteroaryl, wherein any ($C_1$-$C_6$)alkyl, ($C_2$-$C_6$)alkenyl, ($C_3$-$C_8$)cycloalkyl, 6-10 membered aryl, or 5-10 membered heteroaryl of $R^2$ is optionally substituted with one or more (e.g., 1, 2, 3, 4, or 5) halogen or ($C_1$-$C_3$)alkyl;

$R^3$ is H, —C(=O)—$R^{3b}$ or —C(=O)O—$R^{3b}$;

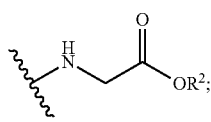

$R^4$ is —$OR^5$ or $R^5$ is H or ($C_1$-$C_6$)alkyl;

each $R^{2a}$ is independently H, ($C_1$-$C_6$)alkyl, ($C_2$-$C_6$)alkenyl, ($C_3$-$C_8$)cycloalkyl, 6-10 membered aryl, or 5-10 membered heteroaryl, wherein any ($C_1$-$C_6$)alkyl, ($C_2$-$C_6$)alkenyl, ($C_3$-$C_8$)cycloalkyl, 6-10 membered aryl, or 5-10 membered heteroaryl of $R^{2a}$ is optionally substituted with one or more (e.g., 1, 2, 3, 4, or 5) halogen or ($C_1$-$C_3$)alkyl;

$R^{1a}$ is H, —C(=O)—$R^{3b}$ or —C(=O)O—$R^{3b}$; and each $R^{3b}$ is independently ($C_1$-$C_6$)alkyl, ($C_2$-$C_6$)alkenyl, ($C_3$-$C_8$)cycloalkyl, 6-10 membered aryl, or 5-10 membered heteroaryl, wherein any ($C_1$-$C_6$)alkyl, ($C_2$-$C_6$)alkenyl, ($C_3$-$C_8$)cycloalkyl, 6-10 membered aryl, or 5-10 membered heteroaryl of $R^{3b}$ is optionally substituted with one or more (e.g., 1, 2, 3, 4, or 5) halo, ($C_1$-$C_3$)alkyl, —OH, —SH, or —NHC(=O)($C_1$-$C_3$)alkyl;

or a salt thereof;

or a compound of formula I wherein $R^1$ is H, $R^4$ is

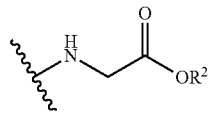

and the compound of formula I is in the form of a DMAE (dimethylaminoethanol) salt.

One embodiment provides a compound of Ia:

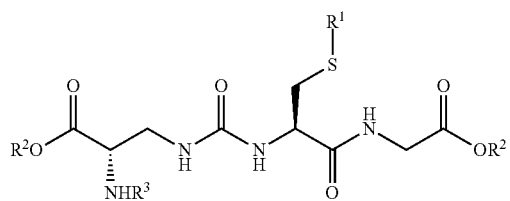

Ia wherein:

$R^1$ is —C(=O)—$R^{1a}$ or —C(=O)O—$R^{1b}$;

$R^{1a}$ is ($C_1$-$C_6$)alkyl, ($C_2$-$C_6$)alkenyl, ($C_3$-$C_8$)cycloalkyl, 6-10 membered aryl, 5-10 membered heteroaryl, a residue of formula IIa or IIb:

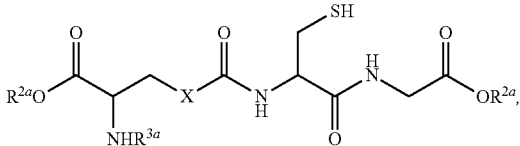

IIa

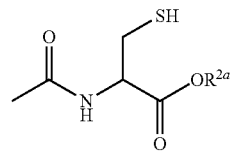

IIb wherein any ($C_1$-$C_6$)alkyl, ($C_2$-$C_6$)alkenyl, ($C_3$-$C_8$)cycloalkyl, 6-10 membered aryl, or 5-10 membered heteroaryl of $R^{1a}$ is optionally substituted with one or more (e.g., 1, 2, 3, 4, or 5) halo, ($C_1$-$C_3$)alkyl, —OH, —SH, or —NHC(=O)($C_1$-$C_3$)alkyl;

X is $CH_2$ or NH;

$R^{1b}$ is ($C_1$-$C_6$)alkyl, ($C_2$-$C_6$)alkenyl, ($C_3$-$C_8$)cycloalkyl, 6-10 membered aryl, or 5-10 membered heteroaryl, wherein any ($C_1$-$C_6$)alkyl, ($C_2$-$C_6$)alkenyl, ($C_3$-$C_8$)cycloalkyl, 6-10 membered aryl, or 5-10 membered heteroaryl of $R^{1b}$ is optionally substituted with one or more (e.g., 1, 2, 3, 4, or 5) halo, ($C_1$-$C_3$)alkyl, —OH, —SH, or —NHC(=O)($C_1$-$C_3$)alkyl;

each $R^2$ is independently H, ($C_1$-$C_6$)alkyl, ($C_2$-$C_6$)alkenyl, ($C_3$-$C_8$)cycloalkyl, 6-10 membered aryl, or 5-10 membered heteroaryl, wherein any ($C_1$-$C_6$)alkyl, ($C_2$-$C_6$)alkenyl, ($C_3$-$C_8$)cycloalkyl, 6-10 membered aryl, or 5-10 membered heteroaryl of $R^2$ is optionally substituted with one or more (e.g., 1, 2, 3, 4, or 5) halogen or ($C_1$-$C_3$)alkyl;

$R^3$ is H, —C(=O)—$R^{3b}$ or —C(=O)O—$R^{3b}$;

each $R^{2a}$ is independently H, ($C_1$-$C_6$)alkyl, ($C_2$-$C_6$)alkenyl, ($C_3$-$C_8$)cycloalkyl, 6-10 membered aryl, or 5-10 membered heteroaryl, wherein any ($C_1$-$C_6$)alkyl, ($C_2$-$C_6$)alkenyl, ($C_3$-$C_8$)cycloalkyl, 6-10 membered aryl, or 5-10 membered heteroaryl of $R^{2a}$ is optionally substituted with one or more (e.g., 1, 2, 3, 4, or 5) halogen or ($C_1$-$C_3$)alkyl;

$R^{3a}$ is H, —C(=O)—$R^{3b}$ or —C(=O)O—$R^{3b}$; and each $R^{3b}$ is independently ($C_1$-$C_6$)alkyl, ($C_2$-$C_6$)alkenyl, ($C_3$-$C_8$)cycloalkyl, 6-10 membered aryl, or 5-10 membered heteroaryl, wherein any ($C_1$-$C_6$)alkyl, ($C_2$-$C_6$)alkenyl, ($C_3$-$C_8$)cycloalkyl, 6-10 membered aryl, or 5-10 membered heteroaryl of $R^{3b}$ is optionally substituted with one or more (e.g., 1, 2, 3, 4, or 5) halo, ($C_1$-$C_3$)alkyl, —OH, —SH, or —NHC(=O)($C_1$-$C_3$)alkyl;

or a salt thereof;

or $R^1$ is H and the compound of formula I is in the form of a DMAE (dimethylaminoethanol) salt.

One embodiment provides a compound of I:

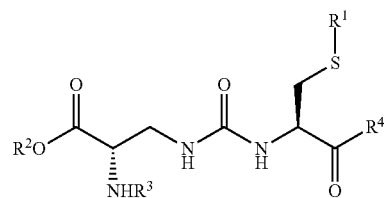

I wherein:

$R^1$ is —C(=O)—$R^{1a}$ or —C(=O)O—$R^{1b}$;

$R^{1a}$ is ($C_1$-$C_6$)alkyl, ($C_2$-$C_6$)alkenyl, ($C_3$-$C_8$)cycloalkyl, 6-10 membered aryl, 5-10 membered heteroaryl, a residue of formula IIa or IIb:

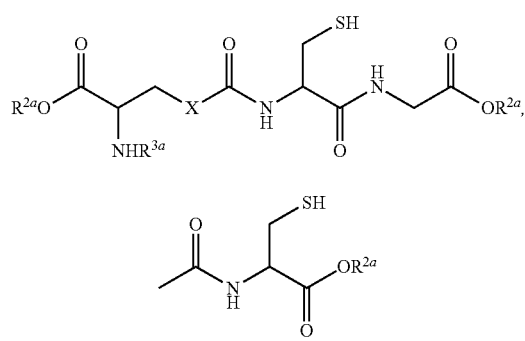

wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{1a}$ is optionally substituted with one or more (e.g., 1, 2, 3, 4, or 5) halo, (C$_1$-C$_3$)alkyl, —OH, —SH, or —NHC(=O)(C$_1$-C$_3$)alkyl;

X is CH$_2$ or NH;

R$^{1b}$ is (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{1b}$ is optionally substituted with one or more (e.g., 1, 2, 3, 4, or 5) halo, (C$_1$-C$_3$)alkyl, —OH, —SH, or —NHC(=O)(C$_1$-C$_3$)alkyl;

each R$^2$ is independently H, (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^2$ is optionally substituted with one or more (e.g., 1, 2, 3, 4, or 5) halogen or (C$_1$-C$_3$)alkyl;

R$^3$ is H, —C(=O)—R$^{3b}$ or —C(=O)O—R$^{3b}$;

R$^4$ is

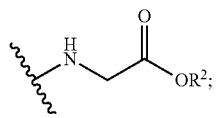

each R$^{2a}$ is independently H, (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{2a}$ is optionally substituted with one or more (e.g., 1, 2, 3, 4, or 5) halogen or (C$_1$-C$_3$)alkyl;

R$^{3a}$ is H, —C(=O)—R$^{3b}$ or —C(=O)O—R$^{3b}$; and each R$^{3b}$ is independently (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{3b}$ is optionally substituted with one or more (e.g., 1, 2, 3, 4, or 5) halo, (C$_1$-C$_3$)alkyl, —OH, —SH, or —NHC(=O)(C$_1$-C$_3$)alkyl;

or a salt thereof.

One embodiment provides a compound of I:

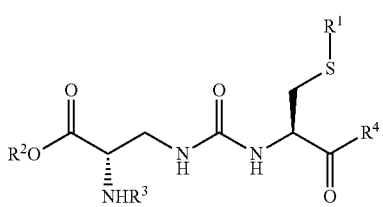

wherein:

R$^1$ is H, —C(=O)—R$^{1a}$, or —C(=O)O—R$^{1b}$;

R$^{1a}$ is (C$_1$-C$_6$)alkyl, (C$_2$-C$_6$)alkenyl, (C$_3$-C$_8$)cycloalkyl, 6-10 membered aryl, 5-10 membered heteroaryl, a residue of formula IIa or IIb:

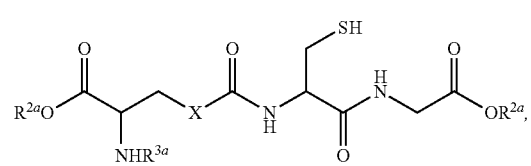

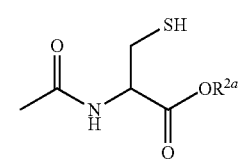

wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{1a}$ is optionally substituted with one or more (e.g., 1, 2, 3, 4, or 5) halo, (C$_1$-C$_3$)alkyl, —OH, —SH, or —NHC(=O)(C$_1$-C$_3$)alkyl;

X is CH$_2$ or NH;

R$^{1b}$ is (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{1b}$ is optionally substituted with one or more (e.g., 1, 2, 3, 4, or 5) halo, (C$_1$-C$_3$)alkyl, —OH, —SH, or —NHC(=O)(C$_1$-C$_3$)alkyl;

each R$^2$ is independently H, (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^2$ is optionally substituted with one or more (e.g., 1, 2, 3, 4, or 5) halogen or (C$_1$-C$_3$)alkyl;

R$^3$ is H, —C(=O)—R$^{3b}$ or —C(=O)O—R$^{3b}$;

R$^4$ is —OR$^5$;

R$^5$ is H or (C$_1$-C$_6$)alkyl;

each R$^{2a}$ is independently H, (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{2a}$ is optionally substituted with one or more (e.g., 1, 2, 3, 4, or 5) halogen or (C$_1$-C$_3$)alkyl;

R$^{3a}$ is H, —C(=O)—R$^{3b}$ or —C(=O)O—R$^{3b}$; and each R$^{3b}$ is independently (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{3b}$ is optionally substituted with one or more (e.g., 1, 2, 3, 4, or 5) halo, (C$_1$-C$_3$)alkyl, —OH, —SH, or —NHC(=O)(C$_1$-C$_3$)alkyl;

or a salt thereof.

One embodiment provides a compound of I:

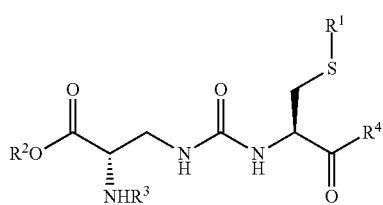

wherein:

R$^1$ is H, —C(=O)—R$^{1a}$ or —C(=O)O—R$^{1b}$;

R$^{1a}$ is (C$_1$-C$_6$)alkyl, (C$_2$-C$_6$)alkenyl, (C$_3$-C$_8$)cycloalkyl, 6-10 membered aryl, 5-10 membered heteroaryl, a residue of formula IIa or IIb:

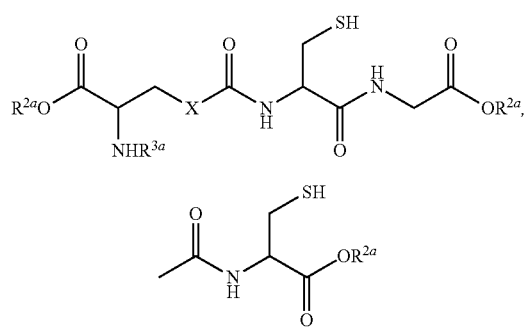

wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{1a}$ is optionally substituted with one or more (e.g., 1, 2, 3, 4, or 5) halo, (C$_1$-C$_3$)alkyl, —OH, —SH, or —NHC(=O)(C$_1$-C$_3$)alkyl;

X is CH$_2$ or NH;

R$^{1b}$ is (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{1b}$ is optionally substituted with one or more (e.g., 1, 2, 3, 4, or 5) halo, (C$_1$-C$_3$)alkyl, —OH, —SH, or —NHC(=O)(C$_1$-C$_3$)alkyl;

each R$^2$ is independently H, (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^2$ is optionally substituted with one or more (e.g., 1, 2, 3, 4, or 5) halogen or (C$_1$-C$_3$)alkyl;

R$^3$ is H, —C(=O)—R$^{3b}$ or —C(=O)O—R$^{3b}$;

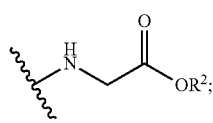

R$^4$ is —OR$^5$ or

R$^5$ is H or (C$_1$-C$_6$)alkyl;

each R$^{2a}$ is independently H, (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{2a}$ is optionally substituted with one or more (e.g., 1, 2, 3, 4, or 5) halogen or (C$_1$-C$_3$)alkyl;

R$^{3a}$ is H, —C(=O)—R$^{3b}$ or —C(=O)O—R$^{3b}$; and each R$^{3b}$ is independently (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{3b}$ is optionally substituted with one or more (e.g., 1, 2, 3, 4, or 5) halo, (C$_1$-C$_3$)alkyl, —OH, —SH, or —NHC(=O)(C$_1$-C$_3$)alkyl;

wherein the compound of formula I is in the form of a DMAE (dimethylaminoethanol) salt.

One embodiment provides a composition prepared by combining a compound of formula I and DMAE (dimethylaminoethanol).

One embodiment provides a method for treating a neurodegenerative disease (e.g., Alzheimer's Disease) in a human (e.g., a human in need thereof), comprising administering a compound of formula I or a pharmaceutically acceptable salt thereof as described herein to the human.

One embodiment provides a compound of formula I or a pharmaceutically acceptable salt thereof as described herein for use in medical therapy.

One embodiment provides a compound of formula I or a pharmaceutically acceptable salt thereof as described herein for the therapeutic or prophylactic treatment of a neurodegenerative disease (e.g., Alzheimer's Disease) in a human (e.g., a human in need thereof).

One embodiment provides the use of a compound of formula I or a pharmaceutically acceptable salt thereof as described in herein for the manufacture of a medicament for the treatment of a neurodegenerative disease (e.g., Alzheimer's Disease).

One embodiment provides processes and intermediates disclosed herein that are useful for preparing compounds of formula I or salts thereof.

BRIEF DESCRIPTION OF FIGURES

FIG. 4A shows the alternation results and FIG. 4B shows the repetitive arm entries results.

FIG. 5A shows the alternation results and FIG. 5B shows the repetitive arm entries results.

FIG. 8A shows the alternation results and FIG. 8B shows the repetitive arm entries results.

FIG. 10A is ratio of arm entries and FIG. 10B is time.

FIG. 11 shows results of Aβ ELISA assay.

DETAILED DESCRIPTION

Figure 1:
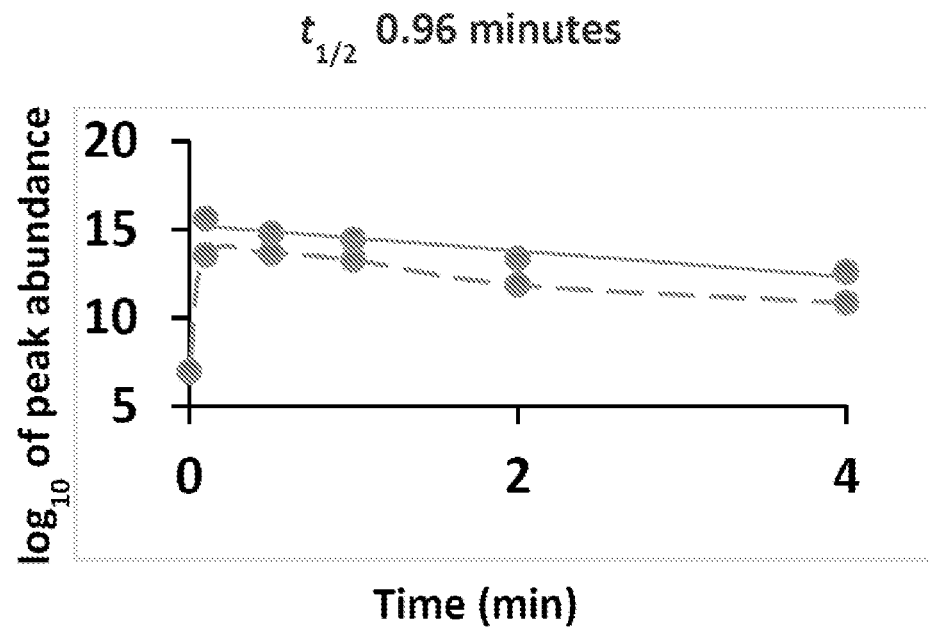
FIG. 1 shows the conversion of compound 4 into p-GSH in the presence of liver homogenate.

Alzheimer's Disease (AD) is an age-related neurodegenerative disorder and mostly characterized by the accumulation of abnormal protein deposits, including amyloid plaques, and loss of neuronal connections within selective brain regions. In previous studies, the metabolically stable p-GSH (pseudo-GSH) was proven to be a stable substrate for the methylglyoxal (MG)-detoxifying enzyme, glyoxalase-I (More S. S., Vince R. ACS Chem Neurosci. 2012 Mar. 21; 3(3):204-10). The deleterious role of MG and the upregulation of glyoxalase I in Alzheimer's-afflicted brain is well established. Certain data has indicated that p-GSH reduced the amyloid-β induced neurotoxicity and prevented cognitive decline in transgenic Alzheimer's mice. Thus, p-GSH may be useful for the treatment of neurodegenerative disorders including AD. Accordingly, alternative derivatives or salts of p-GSH with one or more improved properties such as solubility, permeability, stability, and presystemic metabolism that result in an improved pharmacokinetic profile.

The following definitions are used, unless otherwise described.

The term halo or halogen is fluoro, chloro, bromo, or iodo. Alkyl denotes both straight and branched groups.

As used herein, the term "$(C_a-C_b)$alkyl" wherein a and b are integers refers to a straight or branched chain hydrocarbon radical having from a to b carbon atoms. Thus, when a is 1 and b is 6, for example, the term includes methyl, ethyl, n-propyl, isopropyl, n-butyl, isobutyl, sec-butyl, t-butyl, n-pentyl, and n-hexyl.

The term "alkenyl" refers to an unsaturated alkyl radical having one or more double bonds. Examples of such unsaturated alkyl groups include vinyl, 2-propenyl, crotyl, 2-isopentenyl, 2-(butadienyl), 2,4-pentadienyl, 3-(1,4-pentadienyl) and the higher homologs and isomers.

The term "cycloalkyl" refers to a saturated or partially unsaturated (non-aromatic) all carbon ring having 3 to 8 carbon atoms (i.e., $(C_3-C_8)$carbocycle). The term also includes multiple condensed, saturated all carbon ring systems (e.g., ring systems comprising 2, 3 or 4 carbocyclic rings). Accordingly, carbocycle includes multicyclic carbocycles such as a bicyclic carbocycles (e.g., bicyclic carbocycles having about 3 to 15 carbon atoms, about 6 to 15 carbon atoms, or 6 to 12 carbon atoms such as bicyclo[3.1.0] hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). Non-limiting examples of cycloalkyls include cyclopropyl, cyclobutyl, cyclopentyl, cyclohexyl, bicyclo[2.2.1] heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heteroaryl" as used herein refers to a single aromatic or bicyclic aromatic ring that has at least one atom other than carbon in the ring, wherein the atom is selected from the group consisting of oxygen, nitrogen and sulfur. Thus, "heteroaryl" includes aromatic rings of from about 1 to 9 carbon atoms and about 1-4 heteroatoms selected from the group consisting of oxygen, nitrogen and sulfur. In one embodiment the heteroaryl is a 5-10 membered heteroaryl. In one embodiment the heteroaryl is 5-6 membered monocyclic heteroaryl that includes from about 1-5 carbon atoms and 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term "residue" as it applies to the residue of a compound used herein refers to a compound (e.g., a compound of formula IIa or IIb) that has been modified in any manner which results in the creation of an open valence wherein the site of the open valence is the site wherein the compound is attached to the compound of formula I. The open valence can be created by the removal of 1 or more atoms from the compound (e.g., removal of a single atom such as hydrogen from an SH, acid or amine group). The open valence can also be created by the removal of two or more atoms (e.g., 2, 3, 4, 5, 6, 7, 8, or more) from the compound (e.g., removal of an acid or ester group ($CO_2R^{2a}$) or other groups of two or more atoms). The open valence can vary in location and number of atoms and thus provide a residue of a compound of formula IIa, formula IIb, GSH, p-GSH(pseudo-GSH), or N-acetyl cysteine joined to a compound of formula I.

It is to be understood that the embodiments provided below are for compounds of formula I and that two or more embodiments may be combined.

In one embodiment $R^1$ is —C(═O)—$R^{1a}$ or —C(═O)O—$R^{1b}$ and $R^4$ is

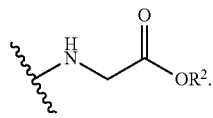

In one embodiment $R^1$ is —C(═O)—$R^{1a}$ or —C(═O)O—$R^{1b}$.

In one embodiment $R^1$ is —C(═O)—$R^{1a}$.

In one embodiment $R^1$ is or —C(═O)O—$R^{1b}$.

In one embodiment $R^{1a}$ or $R^{1b}$ independently methyl, ethyl, or butyl.

In one embodiment $R^{1a}$ and $R^{1b}$ are independently ($C_1$-$C_6$)alkyl.

In one embodiment $R^1$ is —C(═O)$CH_3$, —C(═O)($CH_2$)$_3CH_3$, or —C(═O)O$CH_2CH_3$.

In one embodiment $R^{1a}$ is ($C_1$-$C_6$)alkyl, ($C_2$-$C_6$)alkenyl, ($C_3$-$C_8$)cycloalkyl, 6-10 membered aryl, 5-10 membered heteroaryl, a residue of formula IIa' or IIb':

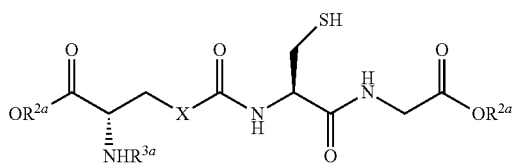

IIa'

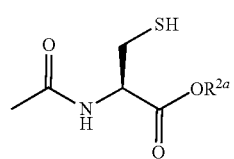

IIb' wherein any ($C_1$-$C_6$)alkyl, ($C_2$-$C_6$)alkenyl, ($C_3$-$C_8$)cycloalkyl, 6-10 membered aryl, or 5-10 membered heteroaryl of $R^{1a}$ is optionally substituted with one or more (e.g., 1, 2, 3, 4, or 5) halo, ($C_1$-$C_3$)alkyl, —OH, —SH, or —NHC(═O)($C_1$-$C_3$)alkyl;

In one embodiment each $R^{1a}$ is independently ($C_1$-$C_6$)alkyl, ($C_2$-$C_6$)alkenyl, ($C_3$-$C_8$)cycloalkyl, 6-10 membered aryl, 5-10 membered heteroaryl,

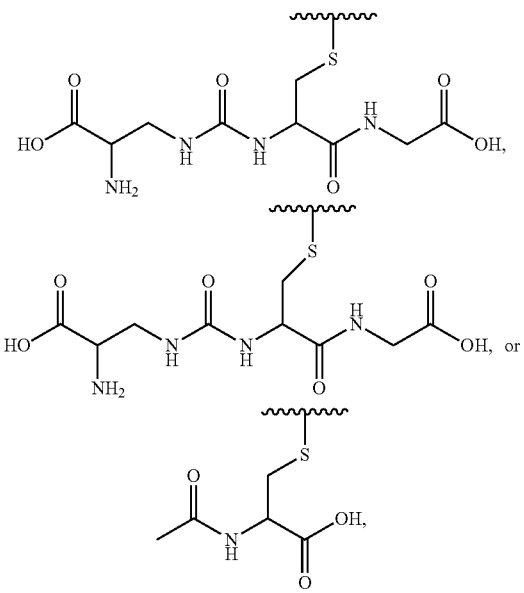

wherein any ($C_1$-$C_6$)alkyl, ($C_2$-$C_6$)alkenyl, ($C_3$-$C_8$) cycloalkyl, 6-10 membered aryl, or 5-10 membered heteroaryl of $R^{1a}$ is optionally substituted with one or more (e.g., 1, 2, 3, 4, or 5) halo, ($C_1$-$C_3$)alkyl, —OH, —SH, or —NHC(═O)($C_1$-$C_3$)alkyl.

In one embodiment each $R^{1a}$ is independently ($C_1$-$C_6$)alkyl, ($C_2$-$C_6$)alkenyl, ($C_3$-$C_8$) cycloalkyl, 6-10 membered aryl, 5-10 membered heteroaryl,

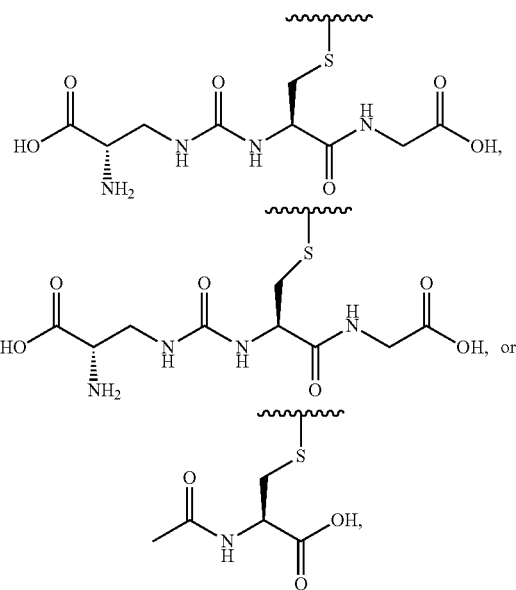

wherein any ($C_1$-$C_6$)alkyl, ($C_2$-$C_6$)alkenyl, ($C_3$-$C_8$) cycloalkyl, 6-10 membered aryl, or 5-10 membered heteroaryl of R[1a] is optionally substituted with one or more (e.g., 1, 2, 3, 4, or 5) halo, ($C_1$-$C_3$)alkyl, —OH, —SH, or —NHC(=O)($C_1$-$C_3$)alkyl.

In one embodiment each R[1a] is independently ($C_1$-$C_6$)alkyl, ($C_2$-$C_6$)alkenyl, ($C_3$-$C_8$)cycloalkyl, 6-10 membered aryl, 5-10 membered heteroaryl,

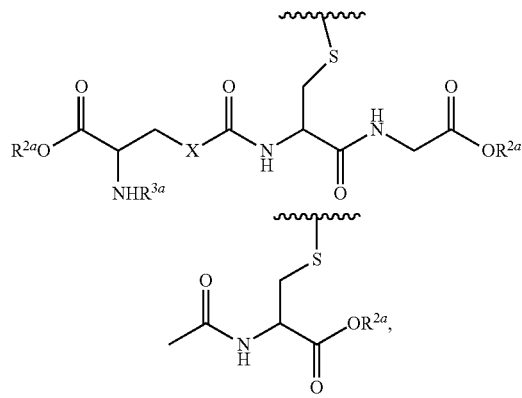

or wherein any ($C_1$-$C_6$)alkyl, ($C_2$-$C_6$)alkenyl, ($C_3$-$C_8$)cycloalkyl, 6-10 membered aryl, or 5-10 membered heteroaryl of R[1a] is optionally substituted with one or more (e.g., 1, 2, 3, 4, or 5) halo, ($C_1$-$C_3$)alkyl, —OH, —SH, or —NHC(=O)($C_1$-$C_3$)alkyl.

In one embodiment each R[1a] is independently ($C_1$-$C_6$)alkyl, ($C_2$-$C_6$)alkenyl, ($C_3$-$C_8$)cycloalkyl, 6-10 membered aryl, 5-10 membered heteroaryl,

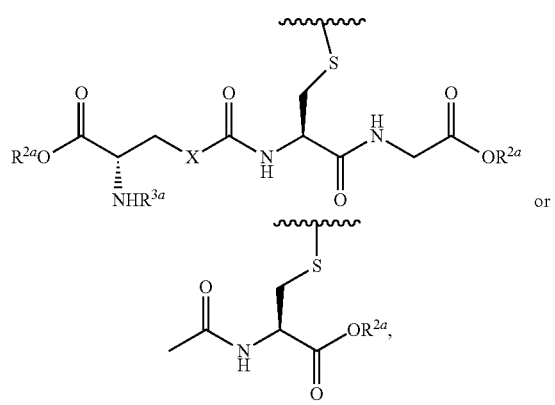

wherein any ($C_1$-$C_6$)alkyl, ($C_2$-$C_6$)alkenyl, ($C_3$-$C_8$)cycloalkyl, 6-10 membered aryl, 5-10 membered heteroaryl is optionally substituted with one or more (e.g., 1, 2, 3, 4, or 5) halo, —OH, —SH, ($C_1$-$C_3$)alkyl, or —NHC(=O)($C_1$-$C_3$)alkyl.

In one embodiment each R[1a] is independently ($C_1$-$C_6$)alkyl, ($C_2$-$C_6$)alkenyl, ($C_3$-$C_8$)cycloalkyl, 6-10 membered aryl, 5-10 membered heteroaryl,

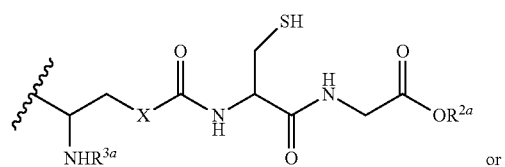

or

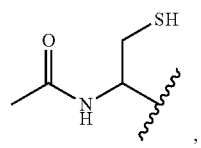

wherein any ($C_1$-$C_6$)alkyl, ($C_2$-$C_6$)alkenyl, ($C_3$-$C_8$)cycloalkyl, 6-10 membered aryl, or 5-10 membered heteroaryl of R[1a] is optionally substituted with one or more (e.g., 1, 2, 3, 4, or 5) halo, —OH, —SH, or —NHC(=O)($C_1$-$C_3$)alkyl.

In one embodiment each R[1a] is independently ($C_1$-$C_6$)alkyl, ($C_2$-$C_6$)alkenyl, ($C_3$-$C_8$)cycloalkyl, 6-10 membered aryl, 5-10 membered heteroaryl,

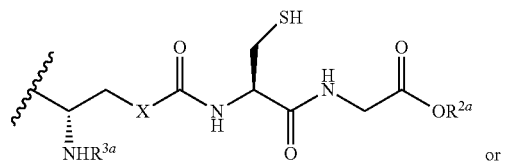

or

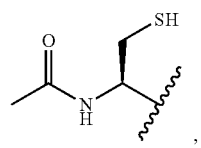

wherein any ($C_1$-$C_6$)alkyl, ($C_2$-$C_6$)alkenyl, ($C_3$-$C_8$)cycloalkyl, 6-10 membered aryl, 5-10 membered heteroaryl of R[1a] is optionally substituted with one or more (e.g., 1, 2, 3, 4, or 5) halo, —OH, —SH, ($C_1$-$C_3$)alkyl, or —NHC(=O)($C_1$-$C_3$)alkyl.

In one embodiment R[1a] (including all R[1a] values discussed herein above) may include a residue of formula IIc:

IIc

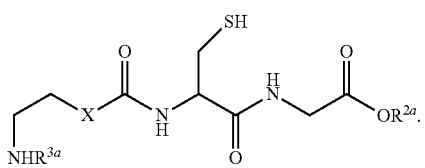

In one embodiment R[1a] (including all R[1a] values discussed herein above) may include a residue of formula IIc':

IIc'

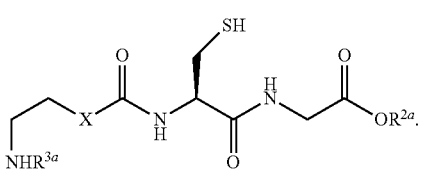

One embodiment provides a compound that is:

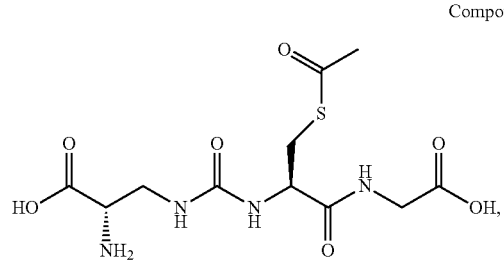

Compound 4

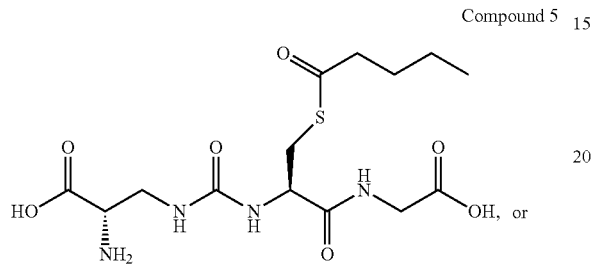

Compound 5

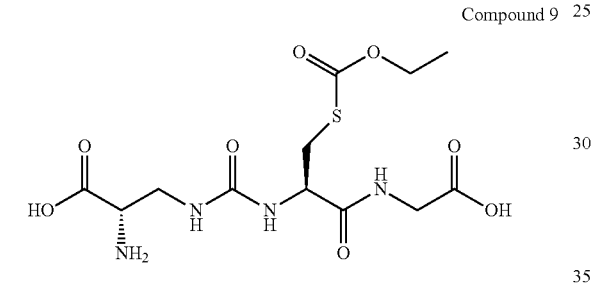

Compound 9 or a salt thereof.

In one embodiment the salt of a compound of formula I comprises DMAE.

In one embodiment the salt of a compound of formula I comprises about 1.8 to about 2.2 molecules of DMAE and 1 molecule of the compound of formula I.

In one embodiment the salt of a compound of formula I comprises about 1.95 to about 2.05 molecules of DMAE and 1 molecule of the compound of formula I.

In one embodiment the salt of a compound of formula I comprises about 2 molecules of DMAE and about 1 of the compound of formula I.

One embodiment provides a salt that is:

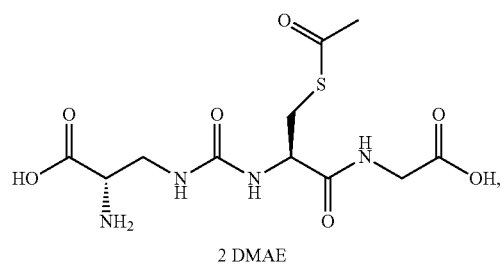

Compound 10

2 DMAE

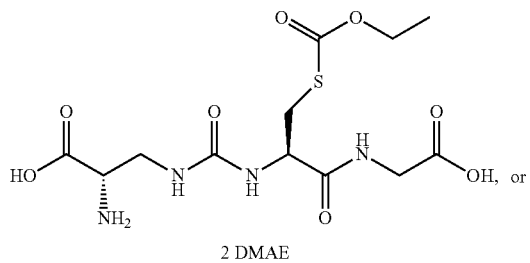

Compound 11

2 DMAE

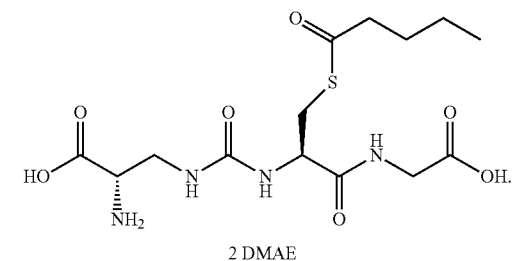

Compound 12

2 DMAE

One embodiment provides a salt of formula I, wherein $R^1$ is H and comprising DMAE (dimethylaminoethanol).

One embodiment provides a compound that is:

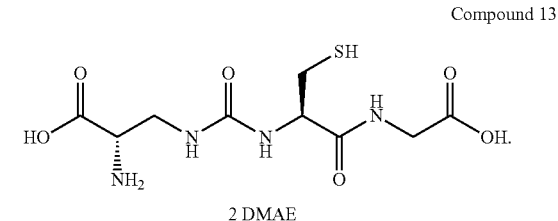 [SMILES: N[C@@H](CNC(=O)N[C@@H](CS)C(=O)NCC(=O)O)C(=O)O]

Compound 13

2 DMAE

One embodiment provides a DMAE salt of:

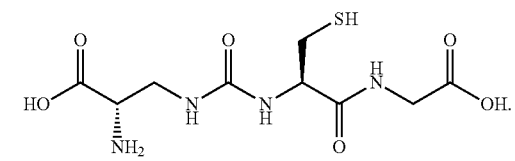 [SMILES: N[C@@H](CNC(=O)N[C@@H](CS)C(=O)NCC(=O)O)C(=O)O]

One embodiment provides a compound that is:

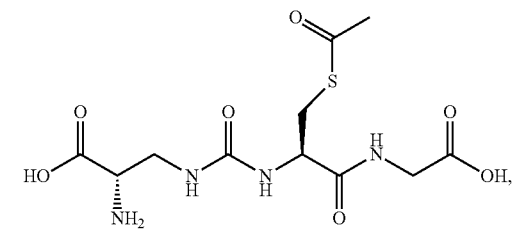

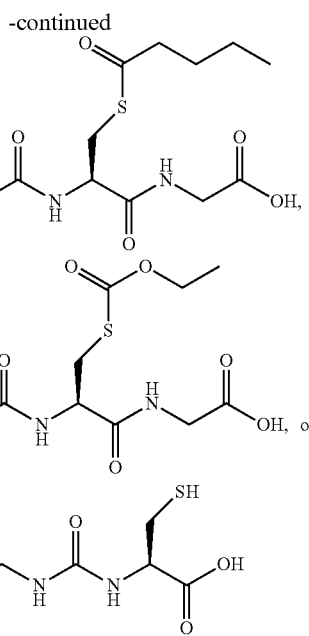

or a salt thereof.

In one embodiment $R^1$ is H, —C(=O)—$R^{1a}$, or —C(=O)O—$R^{1b}$ and $R^4$ is —$OR^5$.

In one embodiment $R^1$ is H.

In one embodiment $R^4$ is —OH.

In one embodiment $R^5$ is H.

One embodiment provides a compound that is:

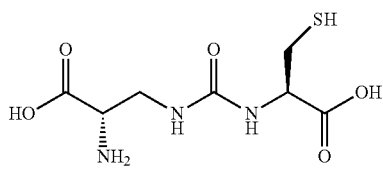 [SMILES: N[C@@H](CNC(=O)N[C@@H](CS)C(=O)O)C(=O)O]

or a salt thereof.

One embodiment provides a compound that is:

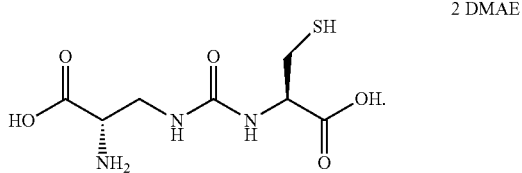 [SMILES: N[C@@H](CNC(=O)N[C@@H](CS)C(=O)O)C(=O)O]

2 DMAE

In one embodiment the salt of a compound of formula I is a pharmaceutically acceptable salt of a compound of formula I.

It will be appreciated by those skilled in the art that compounds described herein having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

It is to be understood that for compounds of the invention when a bond is drawn in a non-stereochemical manner (e.g. flat) the atom to which the bond is attached includes all stereochemical possibilities. It is also to be understood that when a bond is drawn in a stereochemical manner (e.g. bold, bold-wedge, dashed or dashed-wedge) the atom to which the stereochemical bond is attached has the stereochemistry as shown unless otherwise noted.

Accordingly, in one embodiment, a compound of the invention is greater than 50% a single enantiomer. In another embodiment, a compound of the invention is at least 51% a single enantiomer. In another embodiment, a compound of the invention is at least 60% a single enantiomer. In another embodiment, a compound of the invention is at least 70% a single enantiomer. In another embodiment, a compound of the invention is at least 80% a single enantiomer. In another embodiment, a compound of the invention is at least 90% a single enantiomer. In another embodiment, a compound of the invention is at least 95% a single enantiomer. In another embodiment, a compound of the invention is at least 98% a single enantiomer. In another embodiment, a compound of the invention is at least 99% a single enantiomer. In another embodiment, a compound of the invention is greater than 50% a single diastereomer. In another embodiment, a compound of the invention may be at least 51% a single diastereomer. In another embodiment, a compound of the invention is at least 60% a single diastereomer. In another embodiment, a compound of the invention is at least 70% a single diastereomer. In another embodiment, a compound of the invention is at least 80% a single diastereomer. In another embodiment, a compound of the invention is at least 90% a single diastereomer. In another embodiment, the compounds of the invention are at least 95% a single diastereomer. In another embodiment, a compound of the invention is at least 98% a single diastereomer. In another embodiment, a compound of the invention is at least 99% a single diastereomer.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, e.g., orally or parenterally, intranasally by intravenous, intramuscular, topical or subcutaneous routes or in suppository form.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously, intraperitoneally or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day. In certain embodiments, the suitable dosage will be up to about 2 g/kg, which may be formulated in unit dosage form.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds of formula I can be formulated as dermatological compositions and applied to a mammalian host, such as a human by a topical route. For topical administration, the present compounds may be applied in pure form, i.e., when they are liquids. However, it will generally be desirable to administer them to the skin as compositions or formulations, in combination with a dermatologically acceptable carrier, which may be a solid or a liquid. Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Cosmetic compositions may contain conventional ingredients known to those of ordinary skill in the art, such as those described in Kirk-Othmer, Encyclopedia of Chemical Technology, Third Edition (1979), Vol. 7, pages 143-176. In addition, topical preparations and cosmetic formulations may be prepared as described in U.S. Pat. Nos. 4,199,576, 4,136,165, and 4,248,861. Examples of additional useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). The CTFA Cosmetic Ingredient Handbook, Second Edition (1992) describes a wide variety of non-limiting cosmetic and pharmaceutical ingredients commonly used in the skin care industry, which are suitable for use in the articles of the present invention.

The percentage of the compositions and preparations may be varied. In general, a suitable dermatological composition will typically comprise a compound of formula I or a mixture thereof and may conveniently be between about 2-12% of the weight of a dermatological composition. The amount of active compound in such dermatological useful compositions is such that an effective level of compound will be obtained and/or maintained for the desired duration of action.

The compounds of formula I may be useful as glutathione substitutes. Accordingly, the compounds of formula I may be useful for variety applications wherein glutathione has been implicated to have utility. These applications include but are not limited to those applications wherein the use of glutathione imparts a unique property (e.g., anti-oxidant properties). For example, the compounds of formula I may be useful in topical applications such as cosmetics, sunscreens, creams, ointments (e.g., anti-wrinkling ointments) and the like wherein a property such as an anti-oxidant property is desirable.

As glutathione substitutes the compounds of formula I may also be useful in maintaining or improving neural health, for example, by providing an anti-oxidant property. In addition, the compounds of formula I may also be useful as additives to health foods or as nutraceuticals.

Compounds of formula I may also be useful as rescue agents against toxins or poisons that act by virtue of producing oxidative damage to organs. For example, p-GSH is demonstrated to be useful as rescue agent against acetaminophen (ACP) toxicity.

Compounds of formula I, due to their ability to substitute for GSH, may be useful in countering acutely induced oxidative and alkylative damage. An example is acute bronchiolitis obliterans in popcorn factory workers, caused by the flavoring agent, diacetyl.

Toxicity resulting from exposure to radioactivity (expressed as oxidative DNA modification and protein oxidation) has been countered in part by N-acetylcysteine (NAC), which acts by virtue of buttressing GSH levels. Compounds of formula I, by directly substituting for GSH, may be more direct in their address of such toxicities. Similarly, respiratory distress syndromes caused by exposure to volatile electrophiles such as perfluoroisobutene that may occur either occupationally or recreationally due to accidental or planned pyrolysis of polytetrafluoroethene are countered by NAC. Compounds for formula I may be similarly useful.

Deficiency in general leukocyte (lymphocytic or nonspecific neutrophilic) responses in AIDS patients arises in part due to depleted GSH levels. NAC has been previously utilized to counter GSH deficiency. Compounds of formula I, by virtue of their ability to substitute for GSH, may be similarly useful.

Other ailments whose direct or indirect symptoms partly result from GSH depletion or from oxidating insult, such as clinical manifestations of influenza, cancer, heart-disease, Sjogren's syndrome and myoclonous epilepsy, may be ameliorated by treatment with compounds of formula I.

Oxidative insult due to pyrolysis products inhaled during the smoking of cigarette or other fumes causes inflammation of respiratory and oral mucosa. NAC has demonstrated efficacy in countering such harmful effects of smoking; therefore, compounds of formula I that act more directly than NAC may be expected to be useful in such situations.

Erdosteine and other thiols are useful as mucolytic agents due to their thiol functionality. GSH insufflations itself has been utilized to penetrate and reduce respiratory mucosal viscocity. Compounds of formula I have all of the structural characteristics of the aforementioned clinical agents, and therefore may be utile in such cases (Gregory S. Kelly, N. D., "Clinical application of N-acetylcysteine" Alternative Medicine Review, Volume 3, Issue 2, pages 114-127, 1998).

One embodiment provides a composition comprising a compound of formula I or a pharmaceutically acceptable salt thereof in the form of a dermatological composition.

One embodiment provides method for treating a Parkinson's Disease in a human (e.g., a human in need thereof) comprising administering a compound of formula I or a pharmaceutically acceptable salt thereof as described herein to the human.

One embodiment provides a method treating a reperfusion injury in mammal (e.g., a human such as a human in need thereof) comprising administering a compound of formula I or a pharmaceutically acceptable salt thereof as described herein to the mammal.

One embodiment provides a method for treating of amyotrophic lateral sclerosis (ALS), diabetes, acetaminophen toxicity or a stroke in a mammal (e.g., a human such as a human in need thereof) comprising administering a compound of formula I or a pharmaceutically acceptable salt thereof as described herein to the mammal.

One embodiment provides a method for the treatment of amyotrophic lateral sclerosis (ALS) (e.g., a human in need thereof) comprising administering a compound of formula I or a pharmaceutically acceptable salt thereof as described herein to the human.

One embodiment provides a method for the treatment of diabetes in a mammal (e.g., a human such as a human in need thereof) comprising administering a compound of formula I or a pharmaceutically acceptable salt thereof as described herein to the mammal.

One embodiment provides a method for the treatment of acetaminophen toxicity in a mammal (e.g., a human such as a human in need thereof) comprising administering a compound of formula I or a pharmaceutically acceptable salt thereof as described herein to the mammal.

One embodiment provides a method for the treatment of a stroke in a mammal (e.g., a human such as a human in need thereof) comprising administering a compound of formula I or a pharmaceutically acceptable salt thereof as described herein to the mammal.

One embodiment provides a compound of formula I for a composition in the form of a cosmetic, sunscreen or anti-wrinkling composition.

One embodiment provides a compound of formula I wherein the compound of formula I or a salt thereof is administered in the form of a cosmetic, sunscreen or anti-wrinkling composition.

The invention will now be illustrated by the following non-limiting examples.

Example 1

Preparation of Compounds

Preparation of compound 1.

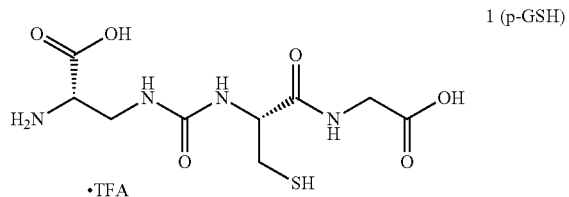 [SMILES: N[C@@H](CNC(=O)N[C@@H](CS)C(=O)NCC(=O)O)C(=O)O]

1 (p-GSH)

The synthesis of compound 1 (p-GSH) has been described in PCT Application Publication WO2013/009647, which document is hereby incorporated by reference in its entirety.

Preparation of Compound 2 and Compound 3.

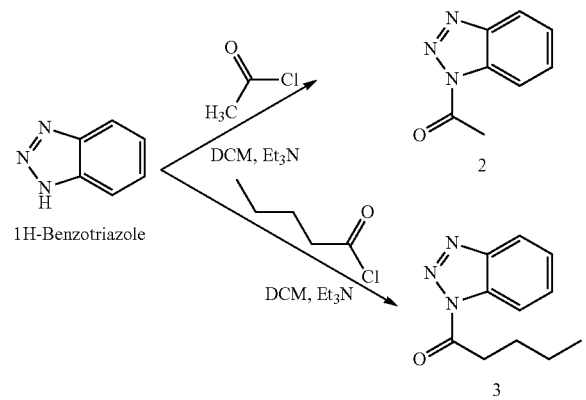

Scheme 1

Preparation of compound 2. Benzotriazole (6.52 g, 54.2 mmol) was dissolved in 50 mL anhydrous methylene chloride, under cooling, added first with mol equivalents of triethylamine (11.06 g, 109.5 mmol) then carefully with 1.1 mol equivalents of acetyl chloride (4.7 g, 60.25 mmol) and stirred for 30 min at room temperature. After the reaction was completed, the mixture was diluted with 50 mL 2 N hydrochloric acid and extracted twice with 25 mL methylene chloride. The combined organic phases were washed twice with 20 mL 2 N hydrochloric acid, twice with 20 mL water and then once with 20 mL saturated sodium chloride solution, dried over sodium sulfate and the solvent was removed. The organic phase was dried over $Na_2SO_4$, then the solvent was removed under reduced pressure to afford compound 2 in quantitative yield. The compound was pure enough to be used for the following step without further treatment. $^1$H NMR (600 Hz, $CDCl_3$): δ (ppm) 8.22-7.93 (m, 2H), 8.02-7.93 (m, 1H), 2.53 (s, 3H); $^{13}$C NMR (150 Hz, $CDCl_3$): 171.1, 145.7, 133.4, 128.2, 115.1, 125.5, 121.3, 23.3; ESI-MS (M+H)$^+$ 162.27.

Preparation of compound 3. Benzotriazole (2.51 g, 21.09 mmol) was dissolved in 50 mL anhydrous methylene chloride, under cooling, added first with mol equivalents of triethylamine (4.47 g, 42.18 mmol) then carefully with 1.1 mol equivalents of valeroyl chloride (2.75 g, 23 mmol) and stirred for 30 min at room temperature. After the reaction was completed, the mixture was diluted with 50 mL 2 N hydrochloric acid and extracted twice with 25 mL methylene chloride. The combined organic phases were washed twice with 20 mL 2 N hydrochloric acid, twice with 20 mL water and then once with 20 mL saturated sodium chloride solution, dried over sodium sulfate and the solvent was removed. The organic phase was dried over $Na_2SO_4$, then the solvent was removed under reduced pressure to afford compound 3 in quantitative yield. The compound was pure enough to be used for the following step without further treatment. $^1$H NMR (600 Hz, $CDCl_3$): δ (ppm) 8.35-8.01 (m, 2H), 7.85-7.75 (m, 1H), 2.73 (t, 2H, J=7.5 Hz), (1.62 (m, 2H), 1.30 (m, 2H), 1.12 (t, 3H, J=6.5 Hz); $^{13}$C NMR (150 Hz, $CDCl_3$): 168.7, 146.7, 131.4, 126.9, 125.3, 120.7, 111.4, 33.5, 27.2, 22.3, 15.1; ESI-MS (M+H)$^+$ 204.32.

Preparation of Compound 4 and Compound 5.

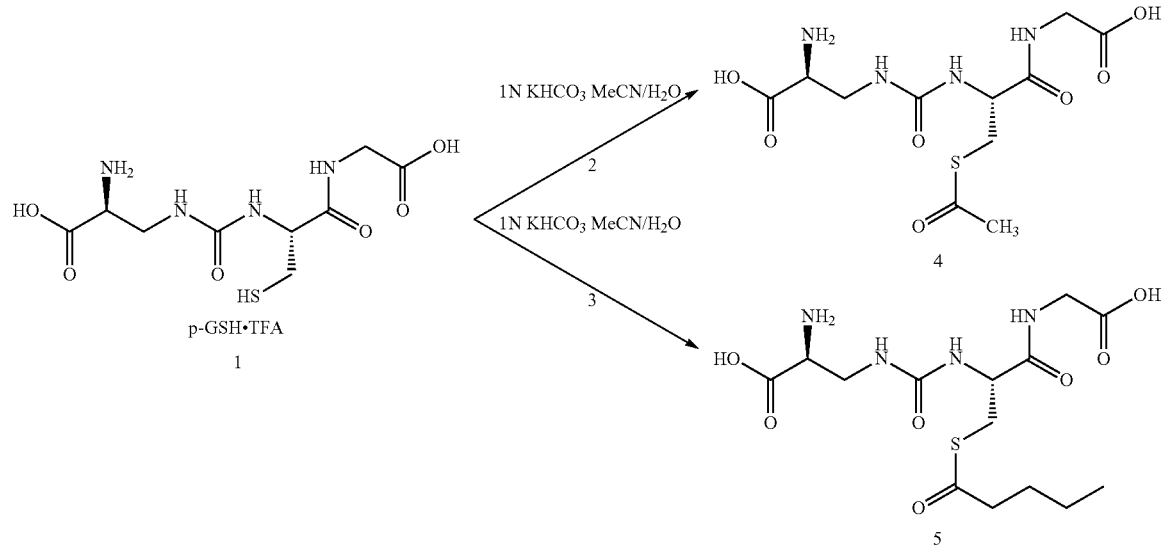

Scheme 2

Preparation of compound 4. A solution of 1-acetyl-1H-benzotriazole (2, 0.525 g, 3.24 mmol) in acetone (20 mL) was added to a solution of p-GSH (0.998 g, 3.24 mmol) in H$_2$O (5 mL) and the reaction mixture was stirred at room temperature for 10 minutes. Then, an aqueous 1N KHCO$_3$ solution (3 mL) was added dropwise to the mixture at 0° C. The reaction progress was monitored by TLC which indicated the completion of the reaction within 1 h. Stirring was continued for 15 minutes, then adjusted to P$^H$ 5 with 1N HCl. The precipitated solid was stirred for 1 h, filtered, washed with acetonitrile, and dried to afford the compound as white solid (0.851 g, 75%). $^1$H NMR (600 MHz, DMSO-d$^6$) δ 4.40-4.35 (m, 1H), 4.13-4.05 (m, 1H), 3.97 (s, 2H), 3.75-3.68 (m, 2H), 3.31 (dd, 1H, J=13.9, 5.2 Hz), 3.15 (dd, 1H, J=14.5, 6.5 Hz), 2.28 (s, 3H). $^{13}$C NMR (150 MHz, DMSO-d$^6$) δ 201.3, 174.2, 173.8, 170.5, 158.6, 54.2, 53.4, 40.9, 39.93, 31.6, 28.2; ESI (M+H)$^+$ 351.23.

Preparation of compound 5. A solution of 1-valeroyl-1H-benzotriazole (2, 0.352 g, 1.73 mmol) in acetone (45 mL) was added to a solution of p-GSH (0.534 g, 1.73 mmol) in H$_2$O (5 mL) and the reaction mixture was stirred at room temperature for 10 minutes. Then, an aqueous 1N KHCO$_3$ solution (3 mL, 165 mg, 1.96 mmol) was added dropwise to the mixture at 0° C. The reaction progress was monitored by TLC which indicated the completion of the reaction within 1 h. Stirring was continued for 15 minutes, then adjusted to P$^H$ 5 with 1N hydrochloric acid. The precipitated solid was stirred for 1 h, filtered, washed with acetonitrile, and dried to obtain the compound as white solid (0.522 g, 76% yield). $^1$H NMR (600 MHz, DMSO-d$^6$) δ 4.85-4.63 (m, 1H), 4.32-4.18 (m, 2H), 4.01-3.93 (m, 2H), 3.59 (dd, 1H, J=13.9, 5.8 Hz), 3.46 (dd, 1H, J=14.9, 6.3 Hz), 3.30 (dd, 1H, J=14.1, 5.3 Hz), 3.12 (dd, 1H, J=13.8, 7.2 Hz), 1.08 (t, 3H, J=7.0 Hz). $^{13}$C NMR (150 MHz, DMSO-d$^6$) δ 174.1, 173.9, 171.9, 172.5, 160.6, 65.8, 54.35, 52.7, 40.8, 39.9, 33.4, 15.5. ESI (M+H)$^+$ 393.31.

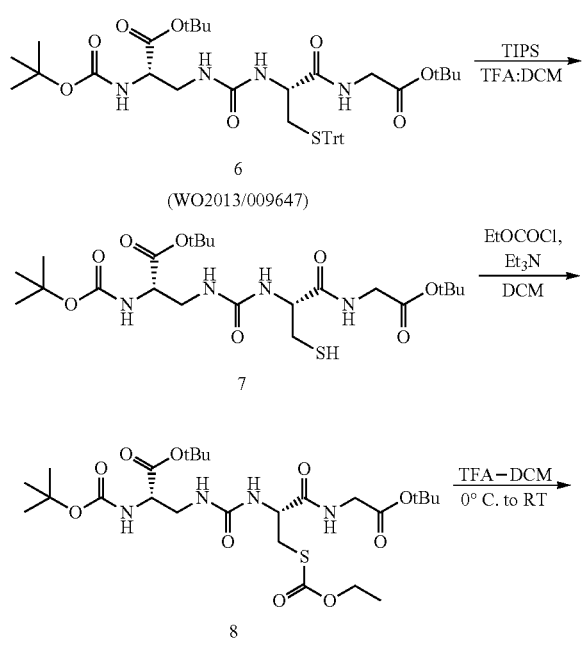

Scheme 3

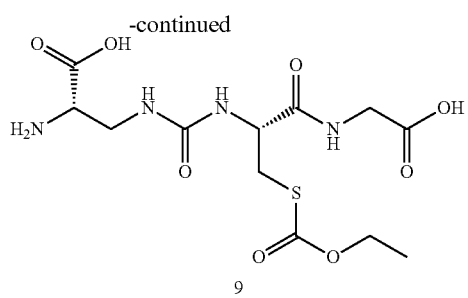

Preparation of compound 7. Compound 6 (0.508 g, 0.65 mmol) (prepared by the method described in PCT Application Publication WO2013/009647) was dissolved in anhydrous methylene (20 ml) at 0° C. TIPS (0.7 mL, 3.3 mmol) and TFA (0.5 mL) was added and the resulting mixture was stirred at 0° C. for 1 h and stirring continued at rt for another 1 h. The reaction mixture was evaporated to obtain the residue as a syrup and was purified by column chromatography and the compound was obtained as a colorless oil (0.231 g, 68%). $^1$H NMR (600 MHz, CDCl$_3$): 7.12 (t, 1H, J=5.8 Hz), 6.10 (brs, 1H), 5.82 (brs, 2H), 4.66 (s, 1H), 4.21 (s, 1H), 3.95-3.89 (m, 2H), 3.67-3.55 (m, 2H), 3.12-2.85 (m, 1H), 2.79 (brs, 1H), 1.66 (t, 1H, J=6.2 Hz), 1.35 (s, 9H), 1.32 (s, 9H), 1.25 (s, 9H). $^{13}$C NMR (150 MHz, CDCl$_3$) δ 172.5, 171.1, 170.6, 156.4, 154.1, 83.2, 81.9, 80.1, 60.8, 56.7, 54.8, 43.5, 29.4, 28.8, 28.1, 26.9, ESI-MS (M+H)$^+$ 521.65.

Preparation of compound 8. Compound 7 (0.205 g, 0.39 mmol) was dissolved in anhydrous methylene chloride (10 ml) and to this was added ethyl chloroformate (41 µL, 0.43 mmol) followed by Et$_3$N (0.1 mL 0.5 mmol). The reaction mixture was stirred overnight at rt. The organic layer was evaporated and EtOAc (30 mL) was added. The organic layer was washed with water, brine and dried over sodium sulfate. The solution was filtered and the residue obtained was purified by column chromatography to afford the product as a colorless oil (0.185 g, 81%). $^1$H NMR (600 MHz, CDCl$_3$) δ 7.76 (s, 1H), 6.35 (d, 1H, J=6.5 Hz), 5.91-5.85 (m, 2H), 4.62 (dd, 1H, J=12.2, 6.8 Hz), 4.37 (brs, 2H), 4.21 (s, 1H), 3.91 (brs, 2H), 3.81-3.72 (m, 2H), 3.31 (dd, 1H, J=13.1, 5.5 Hz), 3.25 (dd, 1H, J=13.6, 7.1 Hz), 1.39 (s, 9H), 1.37 (s, 9H), 1.36 (s, 9H), 1.25 (t, 3H, J=6.8 Hz). $^{13}$C NMR (150 MHz, CDCl$_3$) δ 172.3, 171.8, 170.1, 168.5, 159.2, 156.9, 82.7, 80.6, 64.2, 55.9, 54.8, 42.8, 33.2, 27.4, 26.9, 26.7, 15.7; ESI-MS (M+H)$^+$ 593.41.

Preparation of compound 9. Compound 8 (0.151 g, 0.25 mmol) was dissolved in methylene chloride (10 mL). TFA (10 mL) was added carefully and the resulting mixture was stirred at rt for 6-8 h. The reaction mixture was evaporated to obtain the compound as a light brown solid which was purified using C$_{18}$ silica gel chromatography (0.095 g, 78%). $^1$H NMR (600 MHz, DMSO-d$^6$) δ 4.71-4.47 (m, 1H), 4.35-4.13 (m, 2H), 4.01-3.82 (m, 2H), 3.55 (dd, 1H, J=15.0, 4.2 Hz), 3.37 (dd, 1H, J=15.4, 6.0 Hz), 3.23 (dd, 1H, J=15.7, 5.1 Hz), 3.01 (dd, 1H, J=14.8, 7.2 Hz), 1.25 (t, 3H, J=7.2 Hz); $^{13}$C NMR (150 MHz, DMSO-d$^6$) δ 174.9, 173.1, 172.4, 172.2, 160.6, 65.4, 55.2, 54.7, 42.4, 39.7, 33.5, 14.5; ESI-MS (M+H)$^+$ 381.33.

Scheme 4

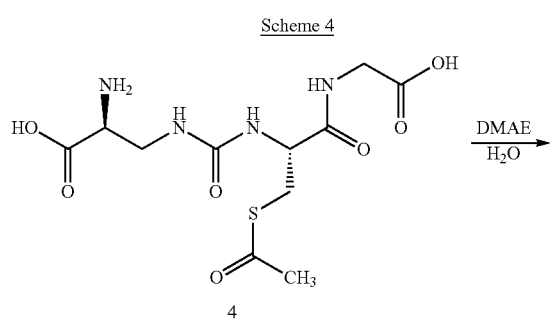

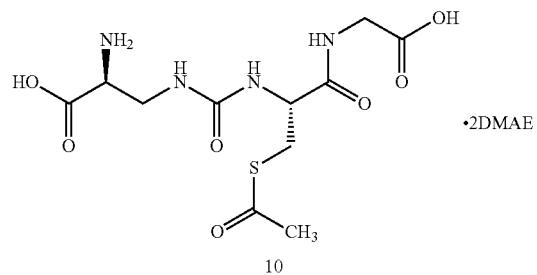

Preparation of compound 10. To a solution of compound 4 (0.574 g, 1.64 mmol) in deionized water (20 mL) was slowly added N, N-dimethylaminoethanol (0.306 g, 3.43 mmol) at rt. The contents were stirred for 1-2 h at rt. The solvent was evaporated to give an off white solid which was washed with diethyl ether (20 mL). The solid was re-dissolved in deionized water and lyophilized to give the compound as an amorphous powder (0.715 g, 84%). $^1$H NMR (600 MHz, D$_2$O) δ 4.81-4.64 (m, 1H), 4.33-4.11 (m, 1H), 4.15 (s, 2H), 3.87-3.71 (m, 2H), 3.42 (m, 2H), 3.23 (dd, 1H, J=14.5, 5.9 Hz), 3.15 (dd, 1H, J=13.8, 6.1 Hz), 2.72 (2H), 2.44 (s, 6H), 2.28 (s, 3H); ESI (M+H)$^+$ 351.35.

Scheme 5

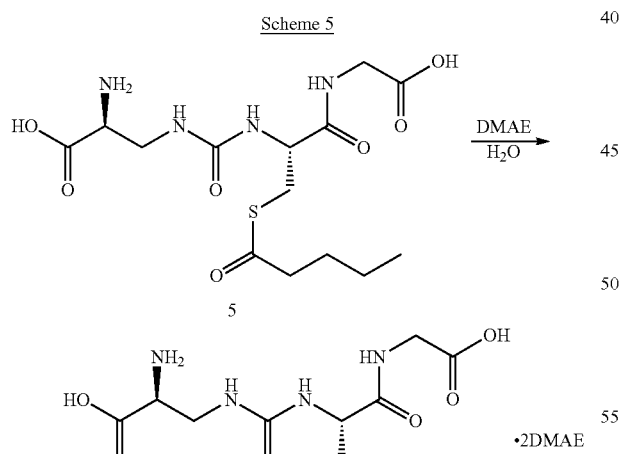

Preparation of compound 11. To a solution of compound 5 (0.501 g, 1.27 mmol) in deionized water (20 mL) was slowly added N, N-dimethylaminoethanol (0.238 g, 2.66 mmol)) at rt. The contents were stirred for 1-2 h at rt. The solvent was evaporated to give an off white solid which was washed with diethyl ether (20 mL). The solid was re-dissolved in deionized water and lyophilized to give the compound as off white powder (0.652 g, 89%). $^1$H NMR (600 MHz, DMSO-d$^6$) δ 5.01-4.86 (m, 1H), 4.57-4.36 (m, 2H), 4.21-3.98 (m, 2H), 3.68 (dd, 1H, J=14.8, 5.1 Hz), 3.75 (dd, 1H, J=15.3, 6.8 Hz), 3.41 (m, 2H), 3.30 (dd, 1H, J=14.5, 5.6 Hz), 3.22 (dd, 1H, J=14.1, 7.0 Hz), 2.81 (m, 2H), 2.41 (s, 6H), 1.08 (t, 3H, J=7.0 Hz); ESI (M+H)$^+$ 393.68.

Scheme 6

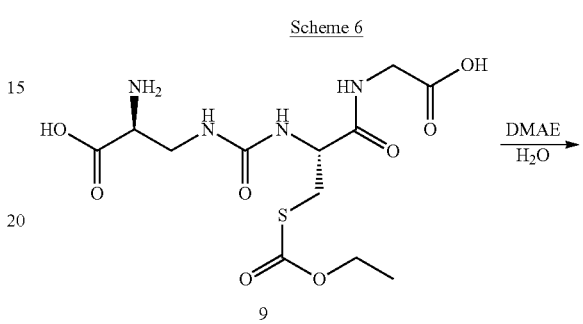

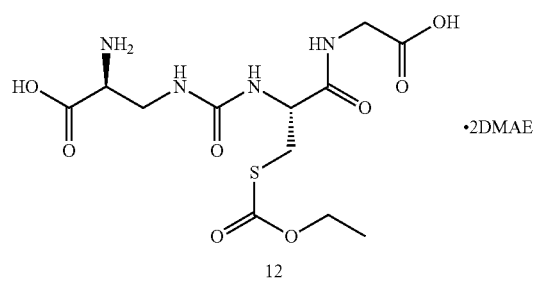

Preparation of compound 12. To a solution of compound 9 (0.615 g, 1.62 mmol) in deionized water (25 mL) was slowly added N, N-dimethylaminoethanol (0.302 g, 3.4 mmol)) at rt. The contents were stirred for 1-2 h at rt. The solvent was evaporated to give an off white solid which was washed with diethyl ether (20 mL). The solid was re-dissolved in deionized water and lyophilized to give the compound as off white powder (0.712 g, 79%). $^1$H NMR (600 MHz, D2O) δ 4.81-4.68 (m, 1H), 4.55-4.38 (m, 2H), 4.15-3.92 (m, 2H), 3.75 (m, 2H), 3.68 (dd, 1H, J=13.8, 4.8 Hz), 3.37 (dd, 1H, J=14.3, 5.7 Hz), 3.33 (dd, 1H, J=15.1, 5.0 Hz), 3.01 (dd, 1H, J=15.4, 6.8 Hz), 2.89 (m, 2H), 2.51 (s, 6H), 1.45 (t, 3H, J=6.8 Hz); ESI-MS (M+H)$^+$ 381.56

Scheme 7

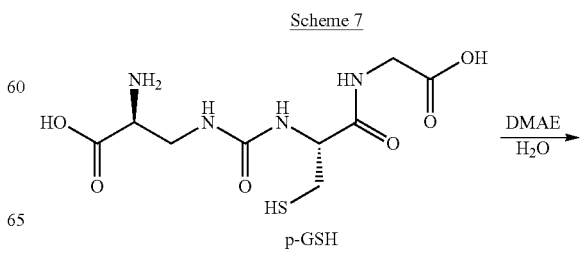

p-GSH

-continued

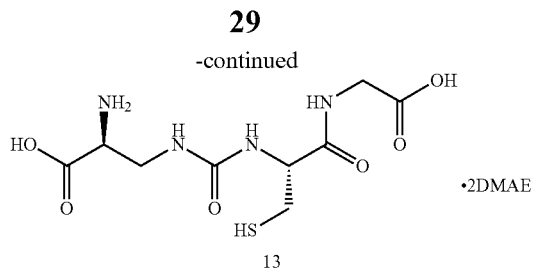

13

Preparation of compound 13. To a solution of p-GSH (0.425 g, 1.38 mmol) in deionized water (20 mL) was slowly added N, N-dimethylaminoethanol (0.258 g, 2.9 mmol)) at rt. The contents were stirred for 1-2 h at rt. The solvent was evaporated to give an off white solid which was washed with diethyl ether (20 mL). The solid was re-dissolved in deionized water and lyophilized to give the compound as off white powder (0.512 g, 76%). $^1$H NMR (600 MHz, D$_2$O): δ 4.65-4.53 (m, 1H), 4.09-4.01 (m, 2H), 3.87-3.79 (m, 1H), 3.75-3.65 (m, 1H), 3.54-3.48 (m, 1H), 2.98-2.85 (m, 2H), 2.72-265 (m, 2H), 2.45 (s, 6H); ESI-MS: [M+H]$^+$ 309.41.

Preparation of Compound 20.

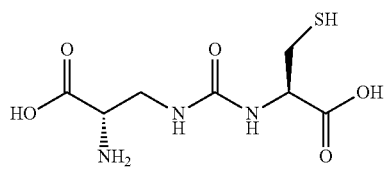

20

Scheme 8

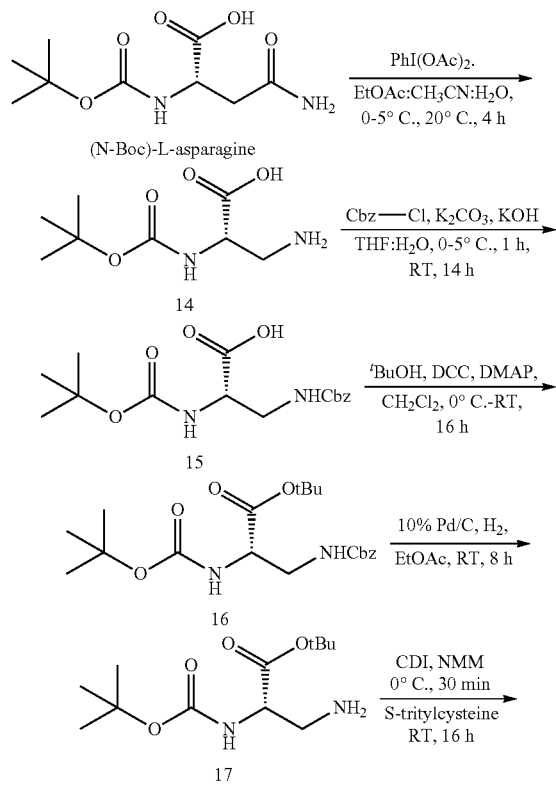

-continued

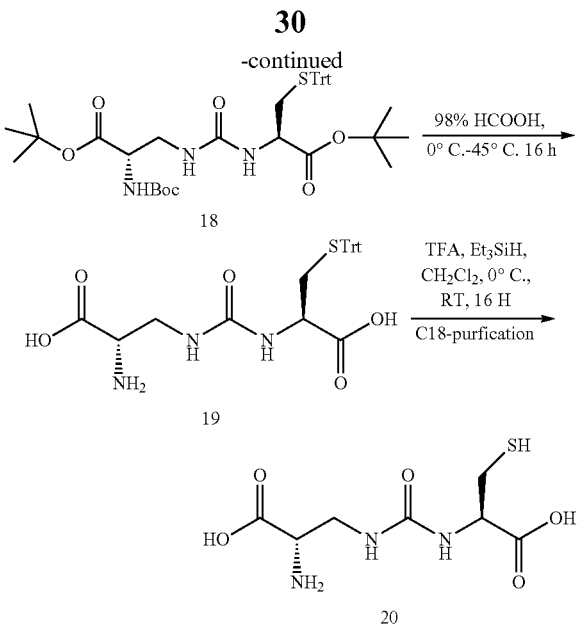

Preparation of compound 14. To a stirring solution of (tert-butoxycarbonyl)-L-asparagine (5.01 g, 21.5 mmol) in a mixture of CH$_3$CN: EtOAc: H$_2$O (2:2:1, 7.5 L) was added (diacetoxyiodo) benzene (8.32 g, 25.8 mmol) at 0-5° C. under inert atmosphere and the reaction mixture was stirred at 20° C. for 4 h. The reaction was monitored by TLC; after completion of the reaction, the reaction mixture was cooled to 0° C., the precipitated solid was filtered, washed with EtOAc (100 mL) and dried under vacuum to afford compound 1 (3.15 g, 72%) as white solid. $^1$H NMR (400 MHz, DMSO-d$_6$): δ 8.04 (br s, 1H), 6.16 (br d, J=4.2 Hz, 1H), 3.66-3.57 (m, 2H), 3.05-2.98 (m, 1H), 2.75-2.68 (m, 1H), 1.39 (s, 9H).

Preparation of compound 15. To a stirring solution of (S)-3-amino-2-((tert-butoxycarbonyl)amino)propanoic acid 1 (2.5 g, 12.2 mmol) in a mixture of THF: H$_2$O (3:1, 4o mL) were added potassium carbonate (3.38 g, 24.5 mmol) and potassium hydroxide (0.68 g, 12.2 mmol) at 0-5° C., followed by addition of benzyl chloroformate (50% in toluene, 6.26 mL, 18.3 mmol) drop wise for 20 min at 0-5° C. and the reaction mixture was stirred at the same temperature for 1 h. The reaction mixture was gradually warmed to RT and stirred for 14 h. The reaction was monitored by TLC; after completion of the reaction, the reaction mixture was diluted with water (15 mL) and washed with Et$_2$O (2×5 mL). The aqueous layer was acidified with citric acid to pH ~4 and extracted with EtOAc (2×25 mL). The combined organic extracts were dried over anhydrous Na$_2$SO$_4$, filtered and concentrated in vacuo to afford compound 2 (380 g, 92%) as colorless syrup. $^1$H NMR (400 MHz, DMSO-d$_6$): δ 12.68 (br s, 1H), 7.42-7.25 (m, 5H), 7.09-6.99 (m, 1H), 5.09-4.93 (m, 2H), 4.11-3.98 (m, 1H), 3.43-3.26 (m, 2H), 1.37 (br d, J=9.9 Hz, 9H).

Preparation of compound 16. To a mixture of N,N'-dicyclohexylcarbodiimide (2.38 g, 11.5 mol), DMAP (68 mG, 0.5 mmol) in CH$_2$Cl$_2$ (30 mL) was added tert-butanol (5.33 mL, 56.2 mmol) at 0-5° C. under inert atmosphere. To this was added (S)-3-(benzyloxy)carbonyl)amino)-2-((tert-butoxycarbonyl) amino) propanoic acid (2) (3.8 g, 11.2 mmol) in CH$_2$C$_{12}$ (10 mL) drop wise for 15 min at 0° C. The reaction mixture was gradually warmed to RT and stirred for 16 h. The reaction was monitored by TLC; after completion of the reaction, the reaction mixture filtered, and the filtrate was washed with 10% aqueous citric acid solution (2×10 mL), saturated NaHCO$_3$ solution followed by brine. The organic layer was separated, dried over anhydrous Na$_2$SO$_4$, filtered and concentrated in vacuo to obtain the crude. The crude material was dissolved in MeOH: H$_2$O (1:1, 30 mL) and extracted with n-hexane (2×50 mL). The combined hexane layers were separated and concentrated in vacuo to afford compound 3 (300 g, crude) as colorless syrup. $^1$H NMR (400 MHz, DMSO-d$_6$): δ 7.44-7.22 (m, 5H), 5.09-4.93 (m, 2H), 4.02-3.94 (m, 1H), 3.93-3.84 (m, 1H), 3.36-3.14 (m, 1H), 1.50-1.31 (m, 18H).

Preparation of compound 17. To a stirring solution of tert-butyl(S)-3-(benzyloxy)carbonyl)amino)-2-((tert-butoxy carbonyl)amino)propanoate 3 (1.6 g) in EtOAc (25 mL) in an autoclave was added 10% Pd/C (50% wet, 0.32 g) at RT under inert atmosphere. The reaction mixture was stirred at RT under hydrogen atmosphere (80 psi) for 8 h. The reaction was monitored by TLC; after completion of the reaction, the reaction mixture was filtered through a pad of celite and the celite bed was eluted with EtOAc (2×15 mL). The filtrate was concentrated in vacuo to afford compound 4 (0.75 g, 65%) as colorless viscous syrup. $^1$H NMR (400 MHz, CDCl$_3$): δ 5.32 (br s, 1H), 4.20-4.16 (m, 1H), 3.09-2.94 (m, 2H), 1.48 (s, 9H), 1.45 (s, 9H). m/z 205.4 [M+H]$^+$.

Preparation of compound 18. To a stirring solution of tert-butyl (S)-3-amino-2-(tert-butoxycarbonyl)amino)propanoate 4 (3.1 g, 11 mmol) in CH$_2$Cl$_2$ (25 mL) under inert atmosphere were added N-methyl morpholine (3 mL, 2.69 mol) and N,N'-dicyclohexylcarbodiimide (18.96 g 0.11 mol) at 0° C. and stirred at the same temperature for 30 min. To this were added S-tritylcysteine (4.25 g, 11 mmol), N-methyl morpholine (3 mL, 2.69 mol) at 0° C. The reaction mixture was gradually warmed to RT and stirred for 16 h. The reaction was monitored by TLC; after completion of the reaction, the reaction mixture was quenched with ice-cold water (100 mL) and the precipitated solid was filtered and dried under vacuum to obtain the crude. The crude was purified through silica gel column chromatography using 25-30% EtOAc/heptanes and further purified by precipitation using methyl tert butyl ether: n-pentane (1:7, 150 mL) to afford compound 5 (4.5 g, 55%) as white solid. $^1$H NMR (400 MHz, DMSO-d$_6$): δ 7.37-7.17 (m, 15H), 7.10-6.97 (m, 1H), 6.59-6.42 (m, 1H), 6.34-6.23 (m, 1H), 4.22-4.04 (m, 1H), 3.92-3.79 (m, 1H), 3.44-3.32 (m, 1H), 3.21-3.09 (m, 1H), 2.47-2.39 (m, 2H), 1.40, 1.38 (s, 18H).

Preparation of compound 19. To a pre-cooled 98% formic acid (10 mL) at 0° C. was added N—(((S)-3-(tert-butoxy)-2-((tert-butoxycarbonyl) amino)-3-oxopropyl)carbamoyl)-S-trityl-L-cysteine (0.540 g, 0.83 mmol) under inert atmosphere and the reaction mixture was gradually warmed to 45° C. and stirred for 16 h. The reaction was monitored by LC-MS; after completion of the reaction, the volatiles were removed in vacuo at 30° C. (water bath temperature) to obtain the crude. The crude was triturated with diethylether (20 mL), CH$_3$CN (25 mL) and dried in vacuo to afford compound 6 (200 mg, 49%) as an off-white solid. $^1$H NMR (400 MHz, DMSO-d$_6$): δ 7.42-7.16 (m, 17H), 6.76-6.69 (m, 1H), 6.68-6.53 (m, 1H), 4.16-4.04 (m, 1H), 3.48-3.28 (m, 1H), 3.27-3.19 (m, 2H), 2.47-2.40 (m, 1H), 2.39-2.30 (m, 1H); m/z 493.7 [M+H]$^+$.

Preparation of compound 20. To a stirring solution of (S)-2-amino-3-(3-((R)-1-carboxy-2-(tritylthio) ethyl) ureido)propanoic acid (0.18 g, 365 mmol) under inert atmosphere in CH$_2$Cl$_2$ was added trifluoroacetic acid (35 mL) dropwise for 20 min at 0° C., followed by addition of triethylsilane (3.5 mL) at 0° C. The reaction mixture was gradually warmed to RT and stirred for 16 h. The reaction was monitored by LC-MS; after completion of the reaction, the volatiles were removed in vacuo at below 20° C. to obtain the crude. The crude was triturated with diethyl ether (50 mL) and dried under vacuum to obtain the solid. The obtained solid was dissolved in water (30 mL, Milli-Q), washed with EtOAc (80 mL). The aqueous layer was lyophilized to afford the crude compound (0.125 g) as an off-white fluffy solid. This compound was dissolved in Milli Q water (20 mL) and lyophilized for 24 h to afford compound (0.095 g) as an off white solid. Reverse phase chromatography was performed with C-18 bound silica gel and eluted with water. Relevant fractions were evaporated and triturated with methanol to give the pseudo-di-peptide (compound 7) as a white solid (0.071 g, 78%). δ 4.57-4.52 (m, 1H), 4.13-4.09 (m, 1H), 3.84-3.77 (m, 1H), 3.73-3.65 (m, 1H), 3.04-3.01 (m, 2H); m/z 251.9 [M+H]$^+$.

Conversion of Compounds 4 and 9 into p-GSH in Liver Homogenate.

Figure 2:
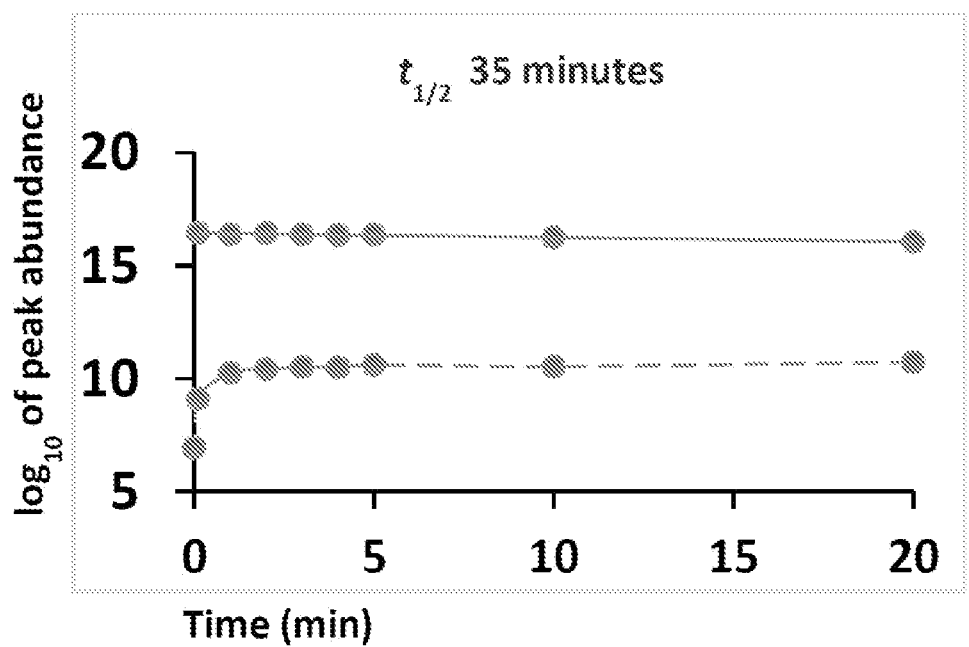
FIG. 2 shows the conversion of compound 9 into p-GSH in the presence of liver homogenate.

The conversion of the p-GSH prodrugs, compounds 4 & 9 into p-GSH were studied in liver homogenate. Liver and brain homogenate were selected because they not only are considered as metabolic organs for p-GSH but also the target organs of p-GSH. The homogenate was prepared from fresh liver tissue and proteinase inhibitors were added in order to prevent degradation of metabolic enzymes. The results of this study are shown in FIGS. 1 and 2. These studies show that the prodrugs (e.g., compounds 4 and 9) can be converted into parent compound p-GSH in the target tissues.

Stability Studies of Compounds 4 and 9.

Compounds 4 and 9 were tested in for stability in the gastrointestinal tract and plasma. Table 1 shows the results of these studies.

|  | Stability in GI tract | | Stability in plasma |
| --- | --- | --- | --- |
|  | Gastric Phase | Intestinal Phase |  |
| p-GSH | >24 h | 1.3 h < 4 h | 2.6 min |
| Compound 4 | >24 h | 5.1 h | 5.8 h |
| Compound 9 | >24 h | 7.7 h | 80 h |

These studies show that the prodrugs (e.g., compounds 4 and 9) are more stable than p-GSH in the GI tract and are more stable in plasma during its distribution to its target organ by systemic circulation.

Memory Test (Spontaneous Alternation T-Maze Test).

Figure 3:
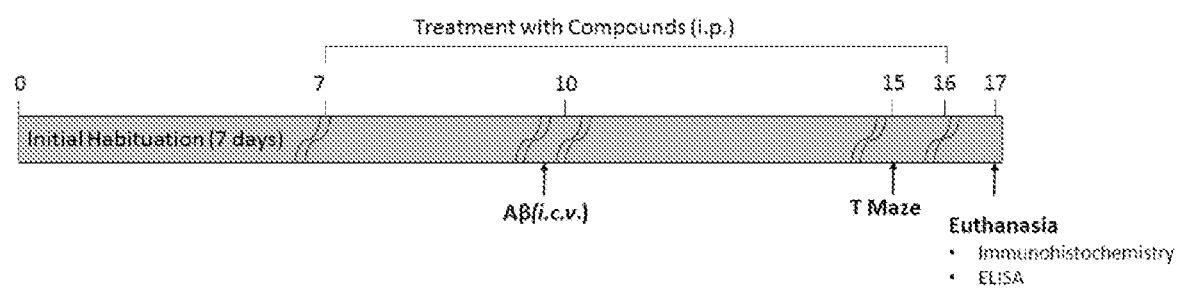
FIG. 3 shows a timeline for the experimental protocol of the Memory Test (spontaneous alternation T-maze test).
Figure 4A:
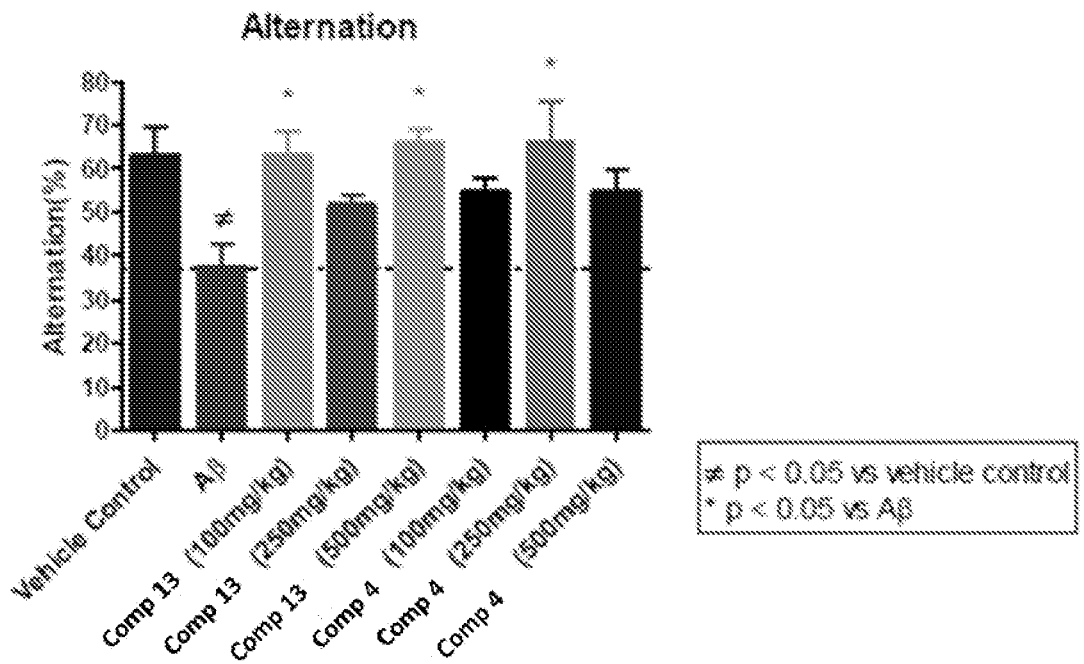
FIG. 4A and FIG. 4B show results of the memory test (spontaneous alternation T-maze test) of compound 4 and compound 13.
Figure 4B:
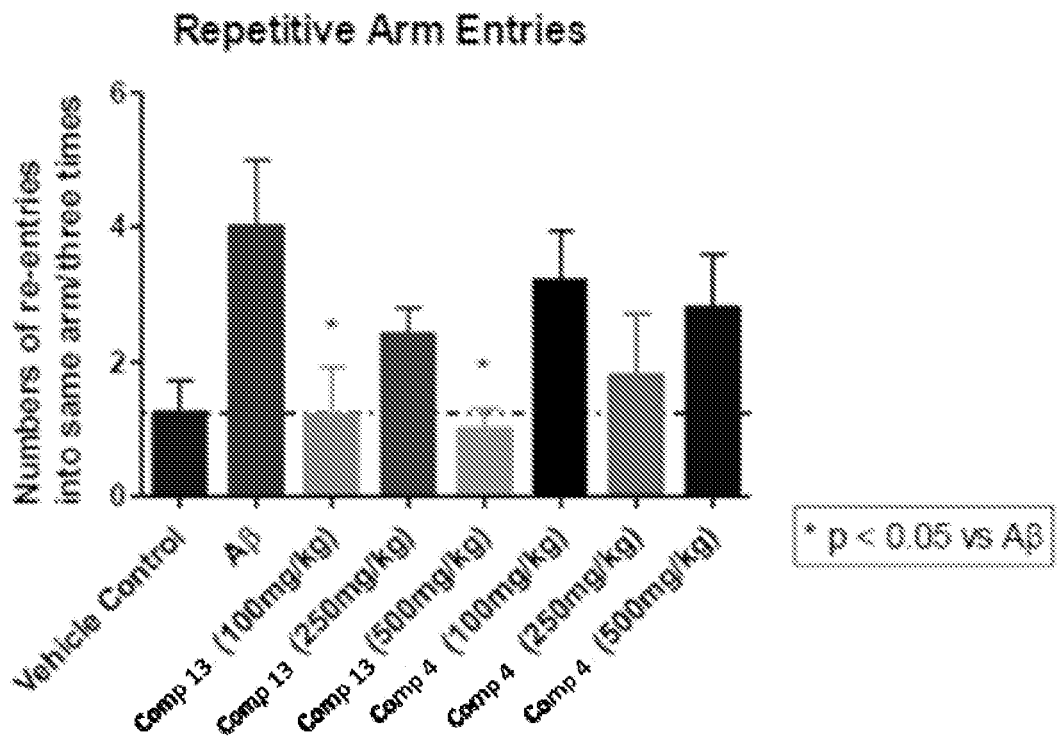
Figure 5A:
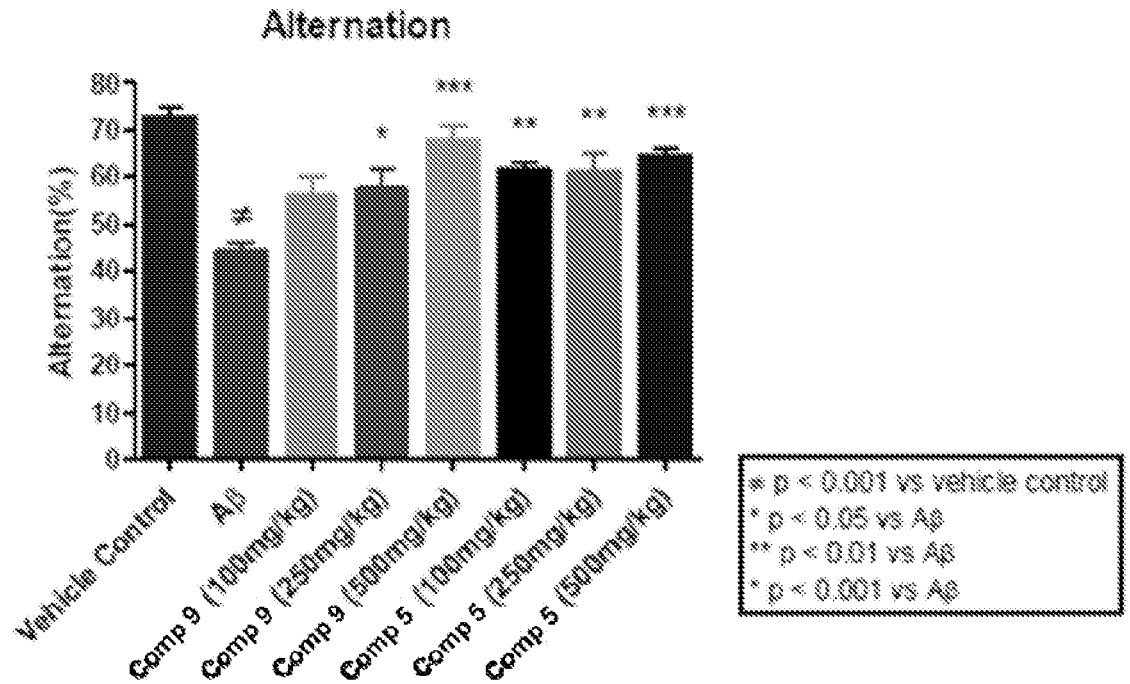
FIG. 5A and FIG. 5B show results of the memory test (spontaneous alternation T-maze test) of compound 9 and compound 5.
Figure 5B:
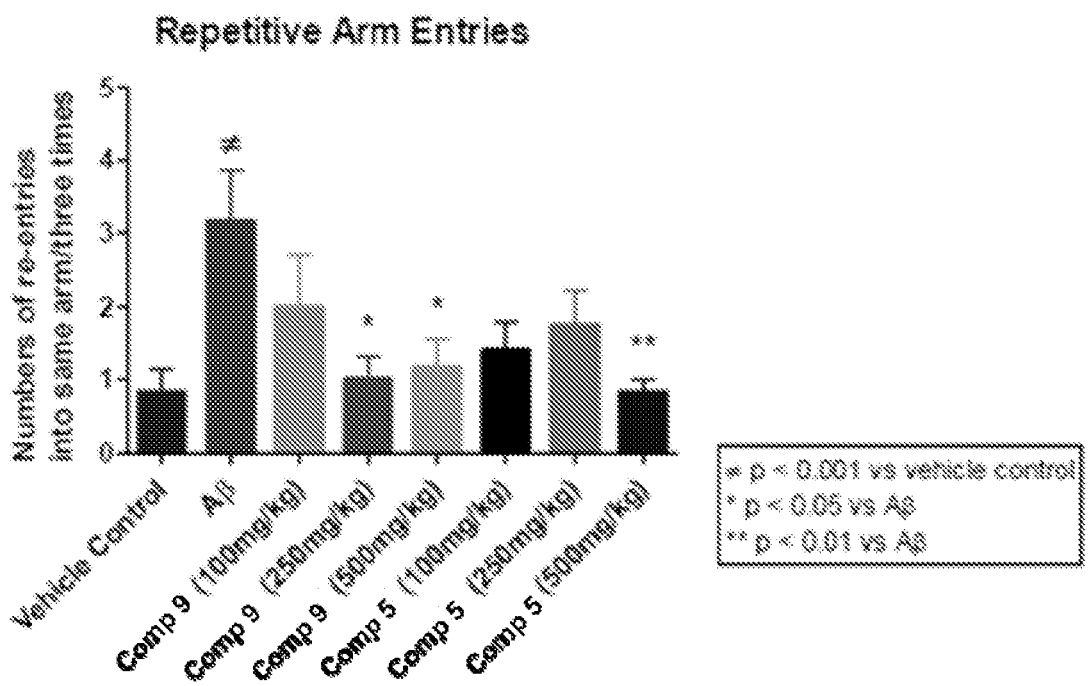
Figure 6:
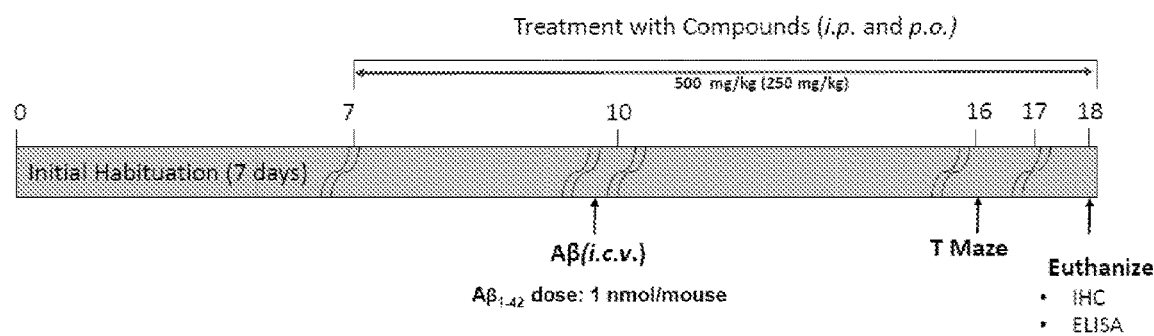
FIG. 6 shows the Aβ-induced mouse model experimental plan. Eight-week-old Wild type C$_{57}$/BL6 mice were treated i.p. and oral with pGSH or its analogs (250 or 300 mg/kg dose) during the entire duration of experiment. The mice were injected with intracerebroventricular (i.c.v) Aβ$_{1-42}$ on day 3 after initiation of drug treatment (1 nmol/mouse). Behavioral test (T-maze) was conducted 6 days after Aβ$_{1-42}$ injection, which was followed by biochemical analysis of brain tissue by ELISA for quantitation of $A\beta_{1-42}$ and immunohistochemical analysis for GFAP (inflammatory marker). The s). Treatment: i.p. and p.o. with compounds and saline for 12 days (250 mg/kg and 500 mg/kg). Groups: Vehicle control & Aβ groups, pGSH (500 mg/kg; p.o.), pGSH_SAC (500 mg/kg; p.o.), pGSH_Dip (500 mg/kg; p.o.), pGSH_Dip (250 mg/kg; i.p.), pGSH_Dip (500 mg/kg; i.p.), N=8.
Figure 7A:
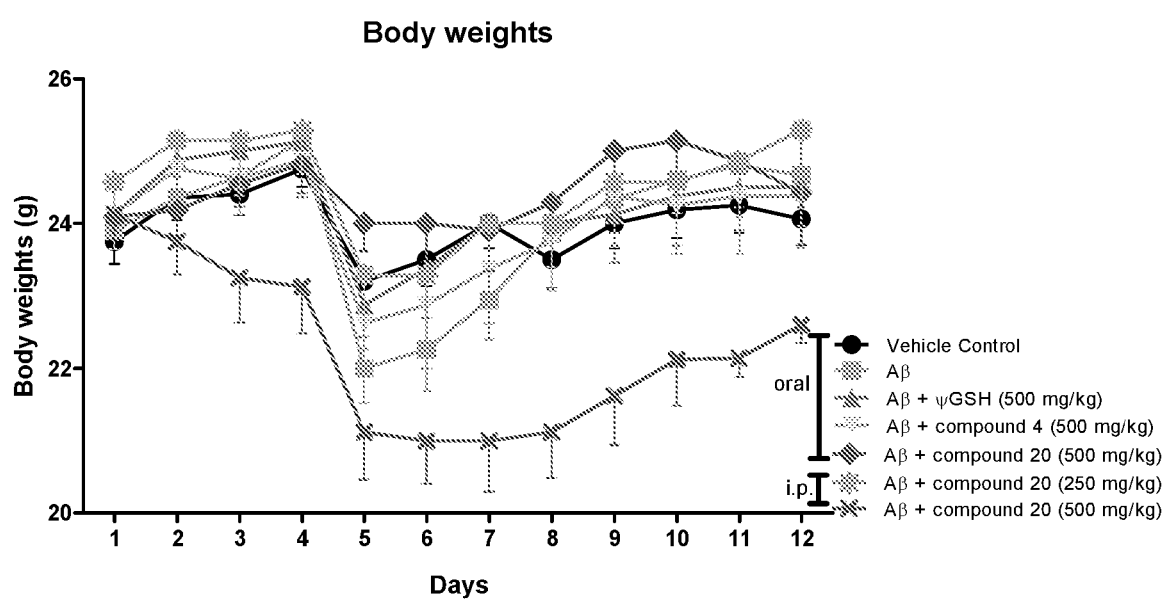
FIG. 7A shows body weights.
Figure 7B:
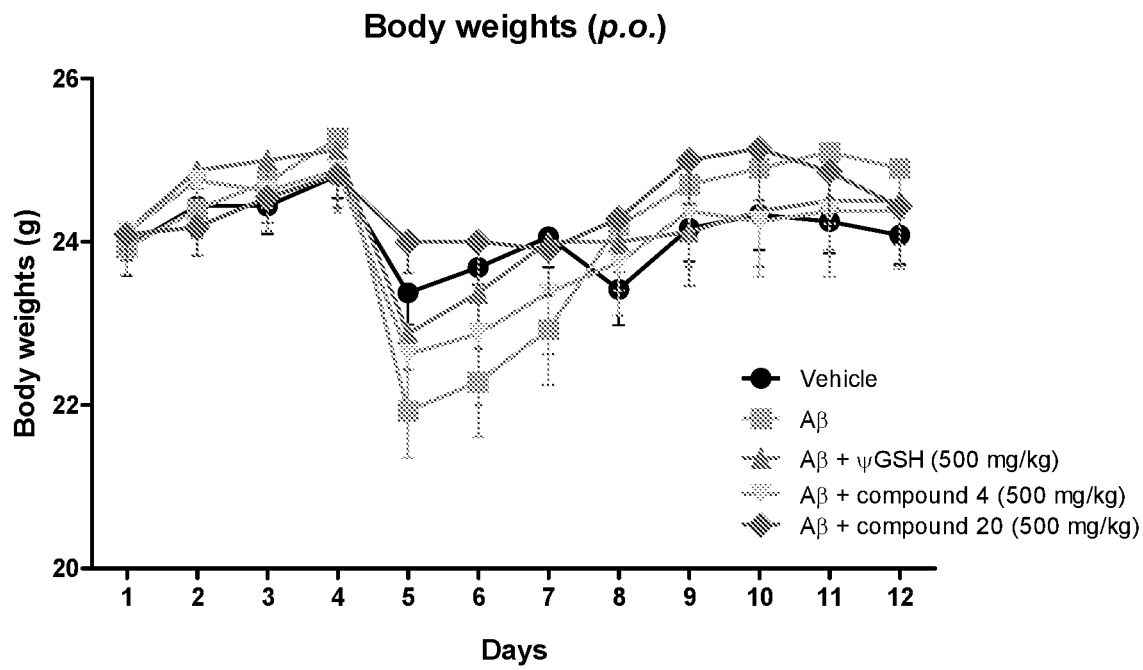
FIG. 7B shows body weights (p.o.)
Figure 7C:
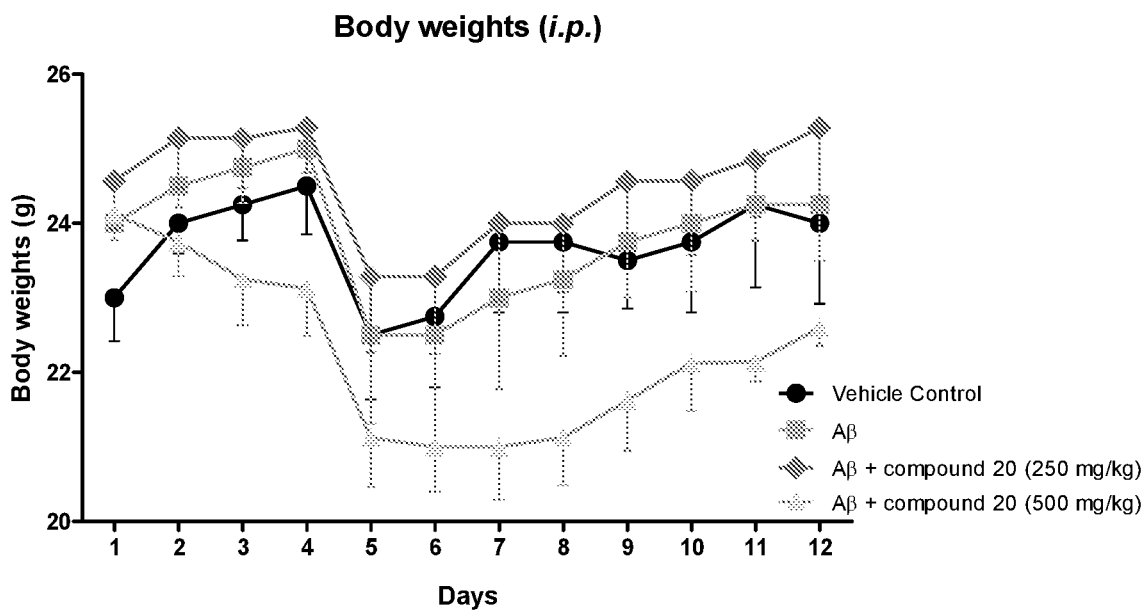
FIG. 7C shows body weights (i.p.)
Figure 8A:
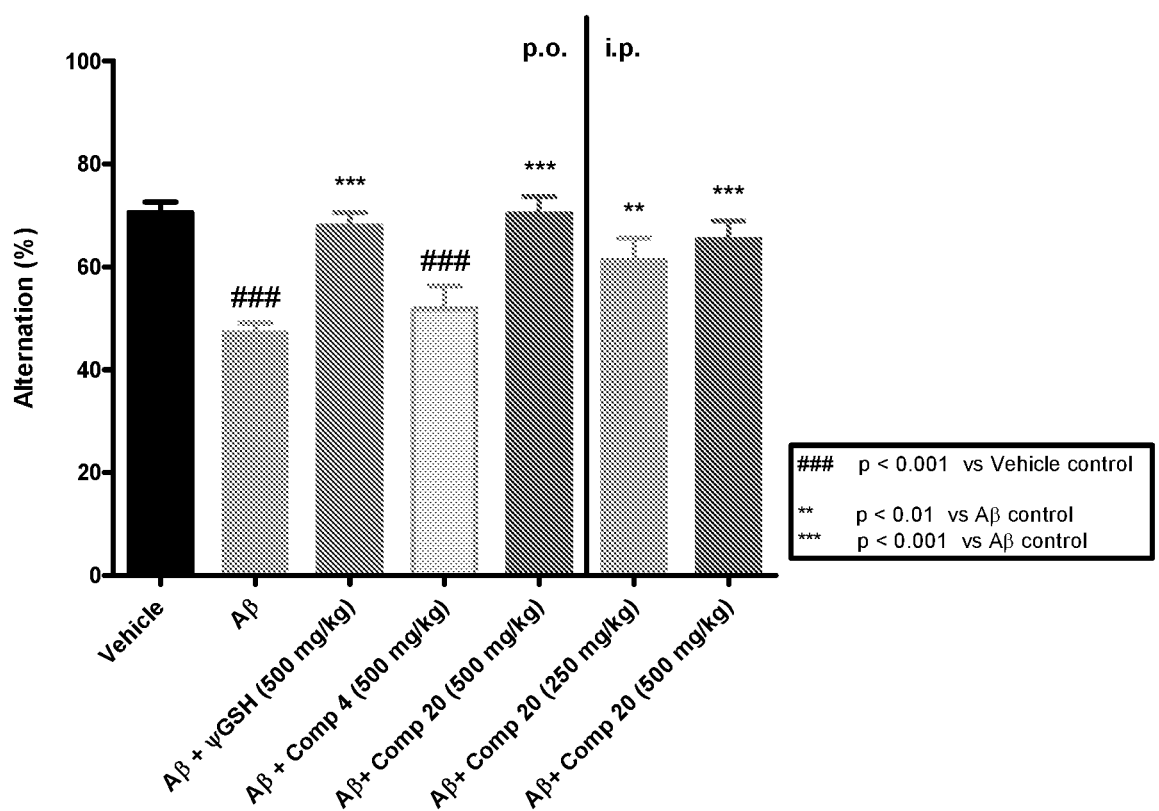
FIG. 8A and FIG. 8B show results of the memory test (spontaneous alternation T-maze test).
Figure 8B:
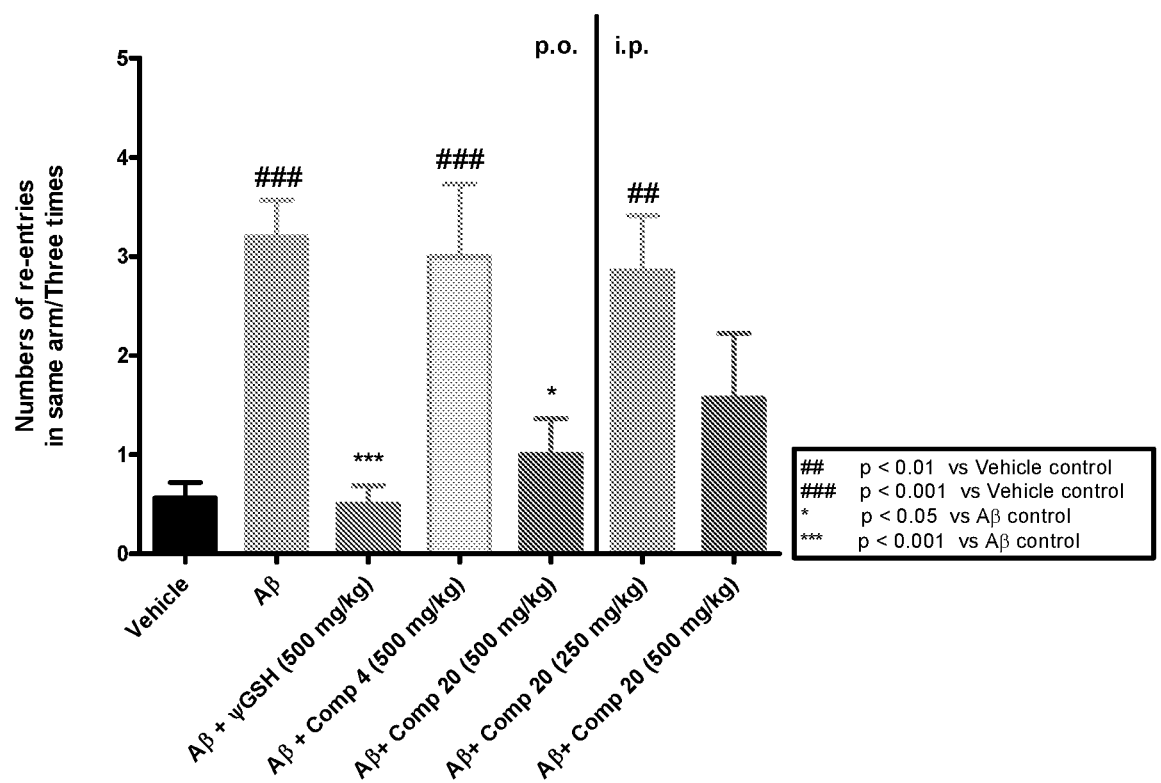
Figure 9:
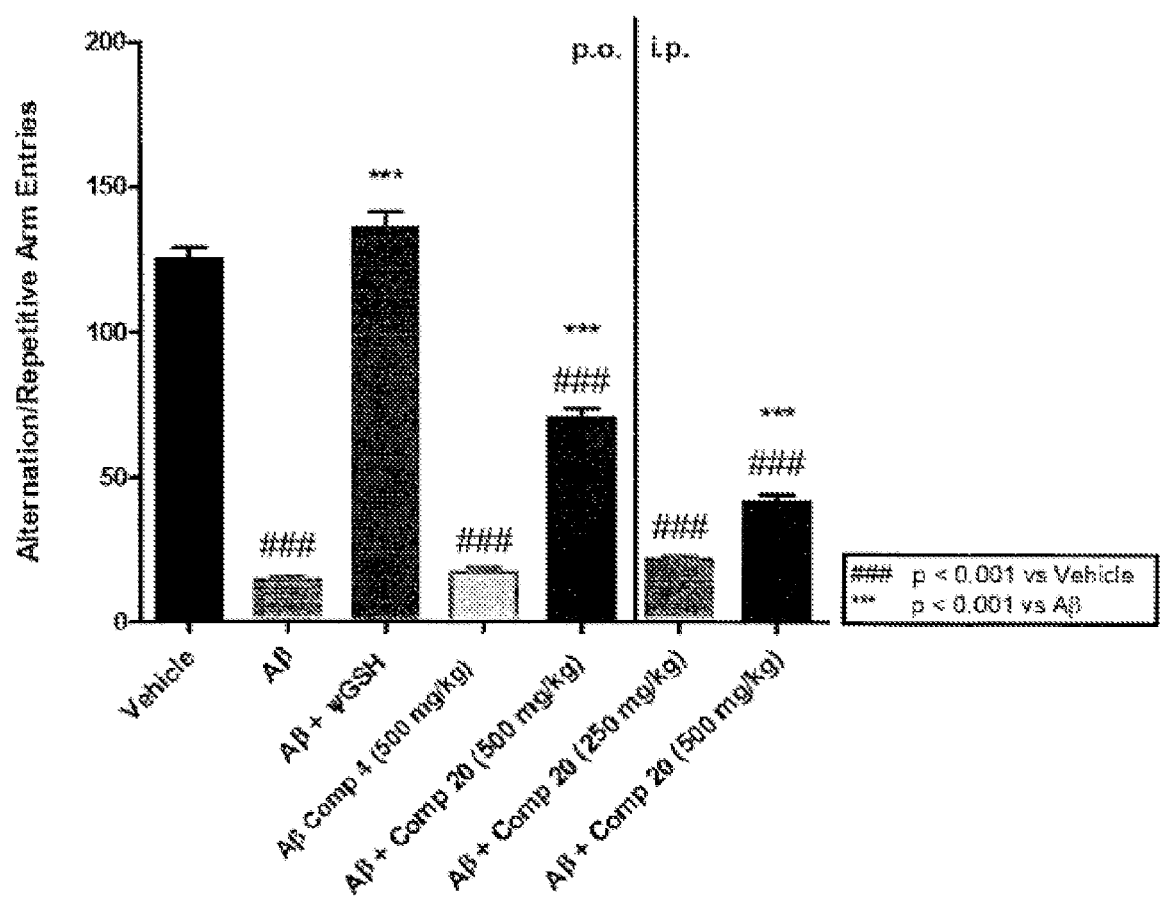
FIG. 9 shows results of the memory test (spontaneous alternation T-maze test; ratio of alternation and repetitive arm entries).
Figure 10A:
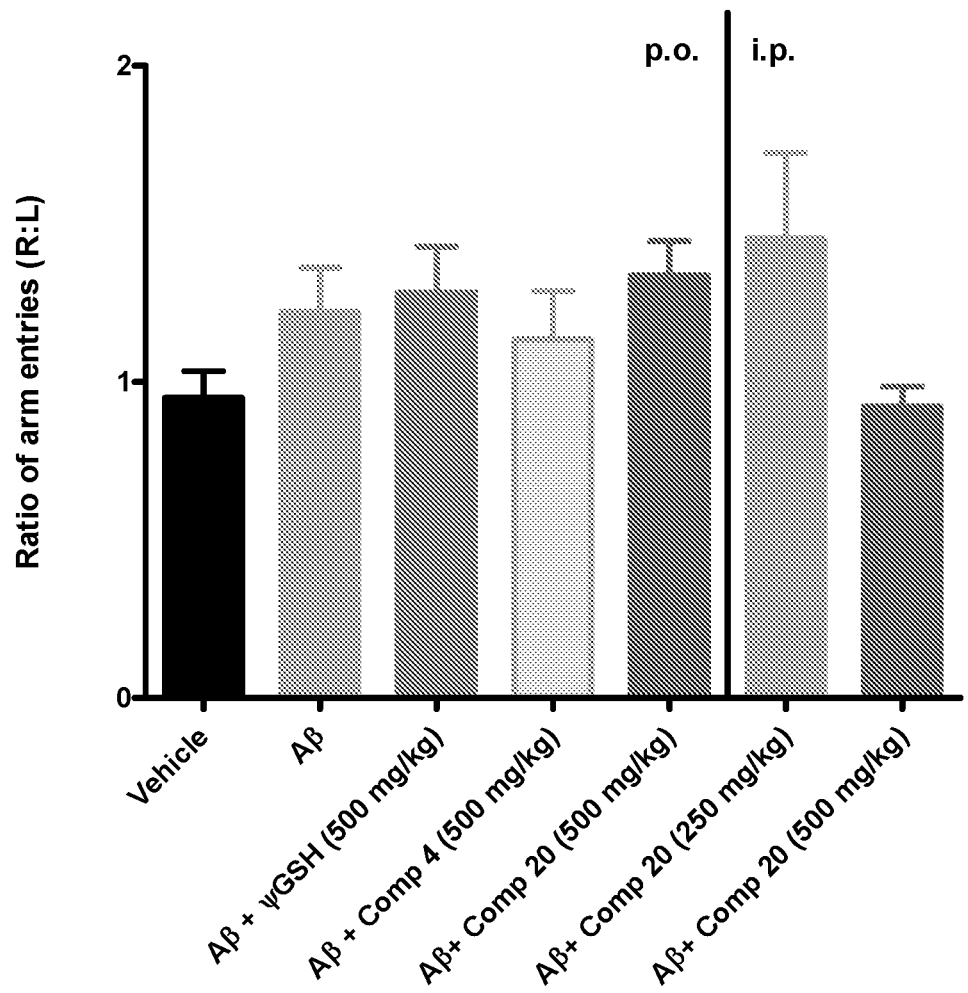
FIG. 10A and FIG. 10B shows results of the T-maze test.
Figure 10B:
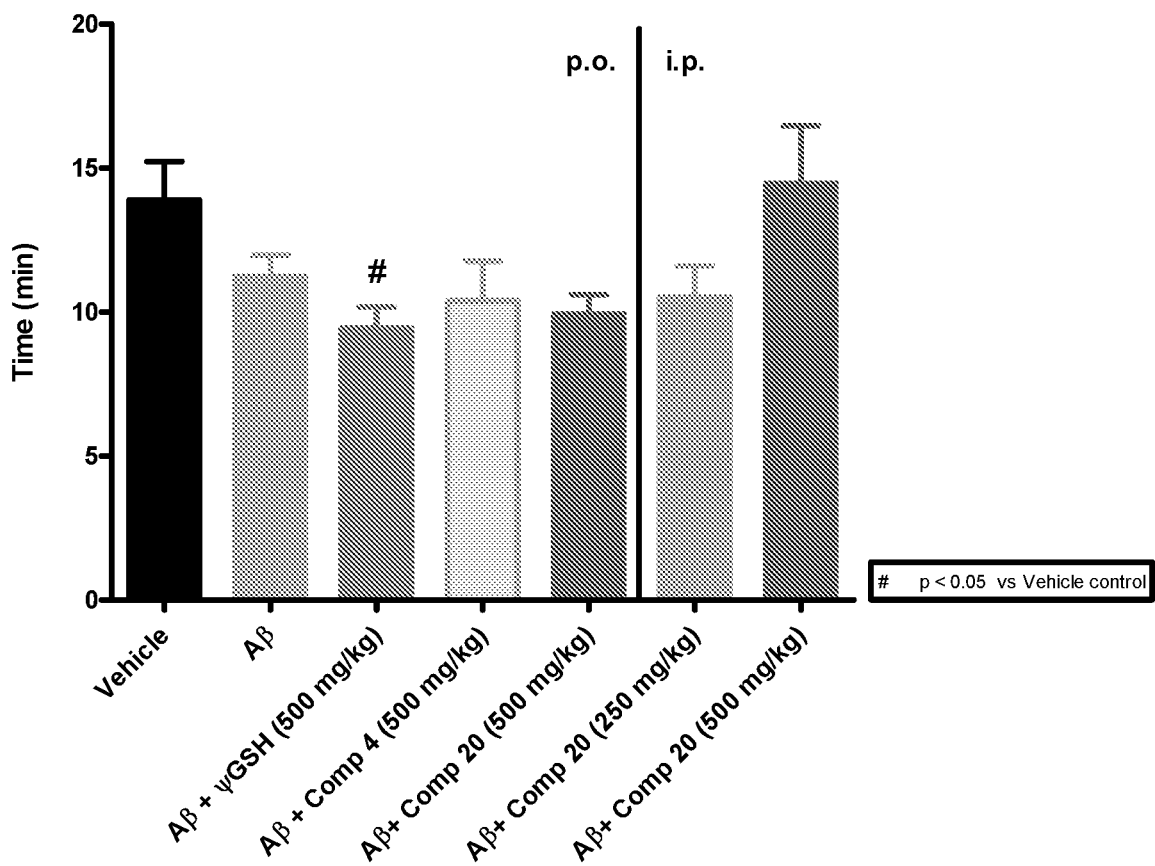
Figure 11A:
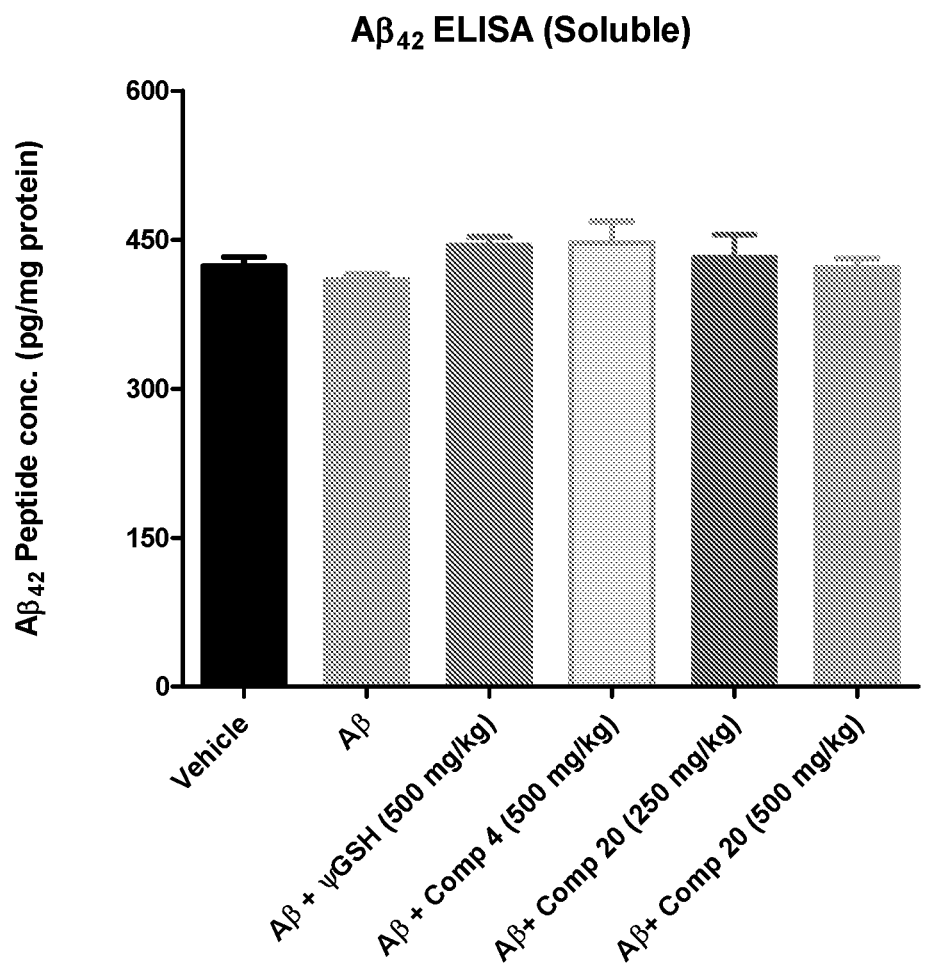
FIG. 11A is $A\beta_{42}$ ELISA (soluble) and FIG. 11B is $A\beta_{42}$ ELISA (insoluble).
Figure 11B:
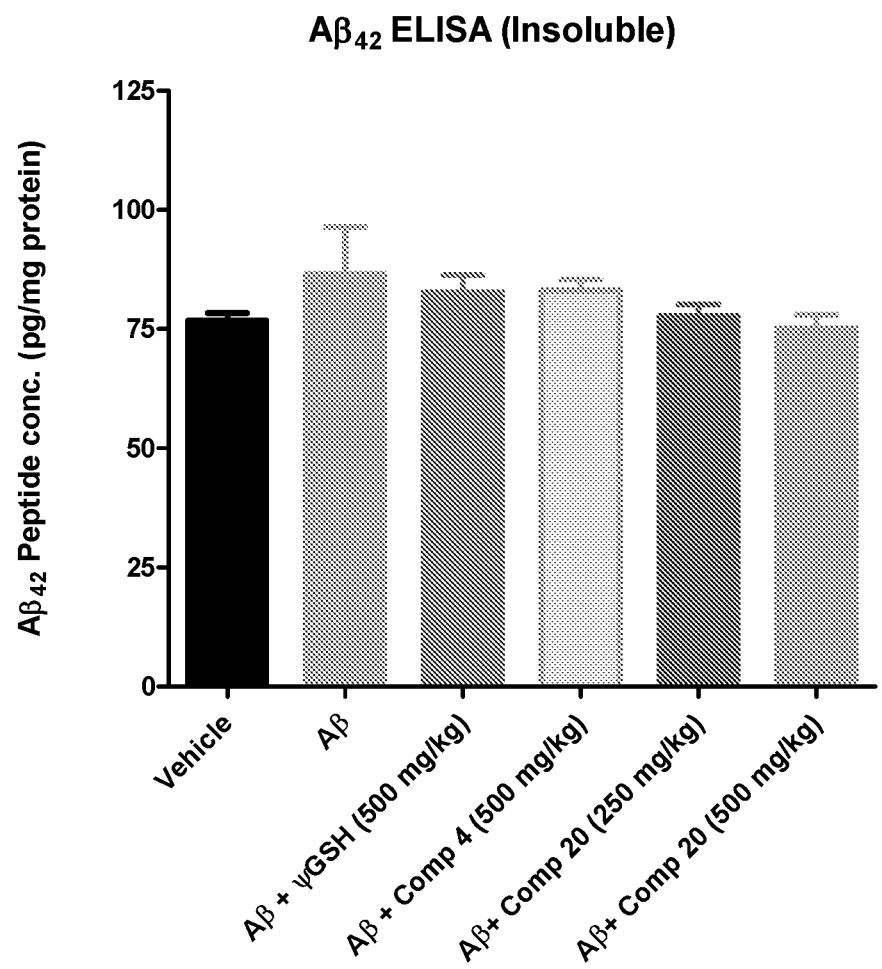
Figure 12:
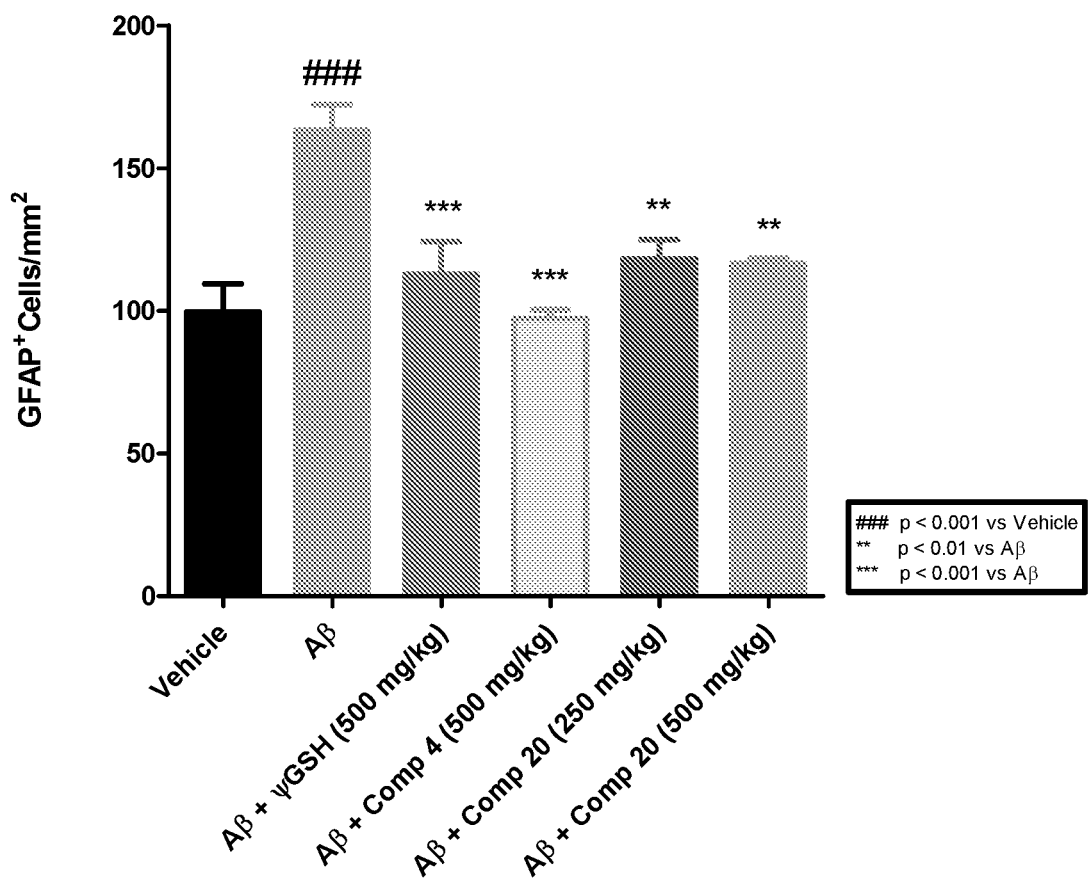
FIG. 12 shows the quantitative analysis of an inflammation marker in the hippocampus of mice treated with compounds
Figure 13A:
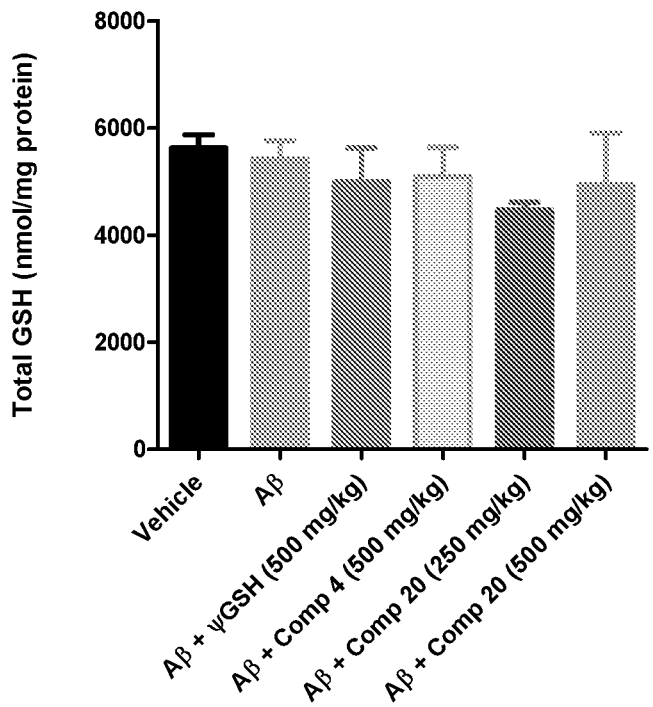
FIG. 13A shows total GSH; 13B shows oxidized GSH (GSSG); 13C shows reduced GSH levels; and 13D shows the ratio of reduced and oxidized GSH (GSH/GSSG).
Figure 13B:
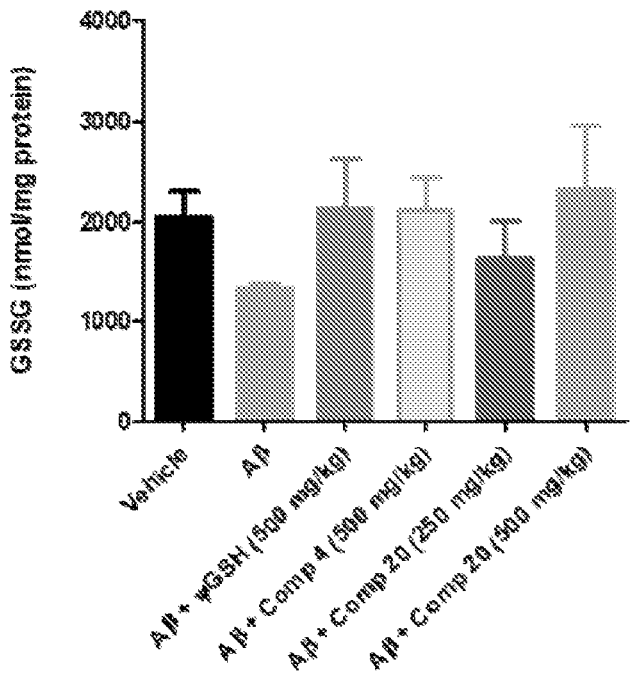
FIG. 13 shows the measurement of glutathione levels in the hippocampus of mice treated with compounds.
Figure 13C:
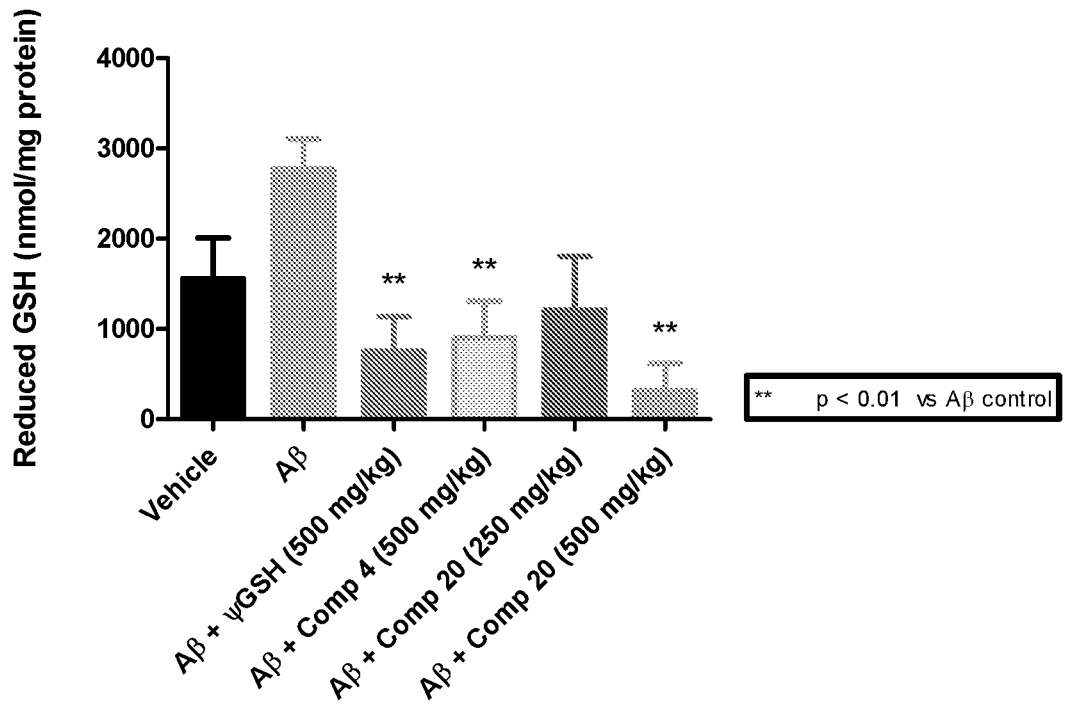
Figure 13D:
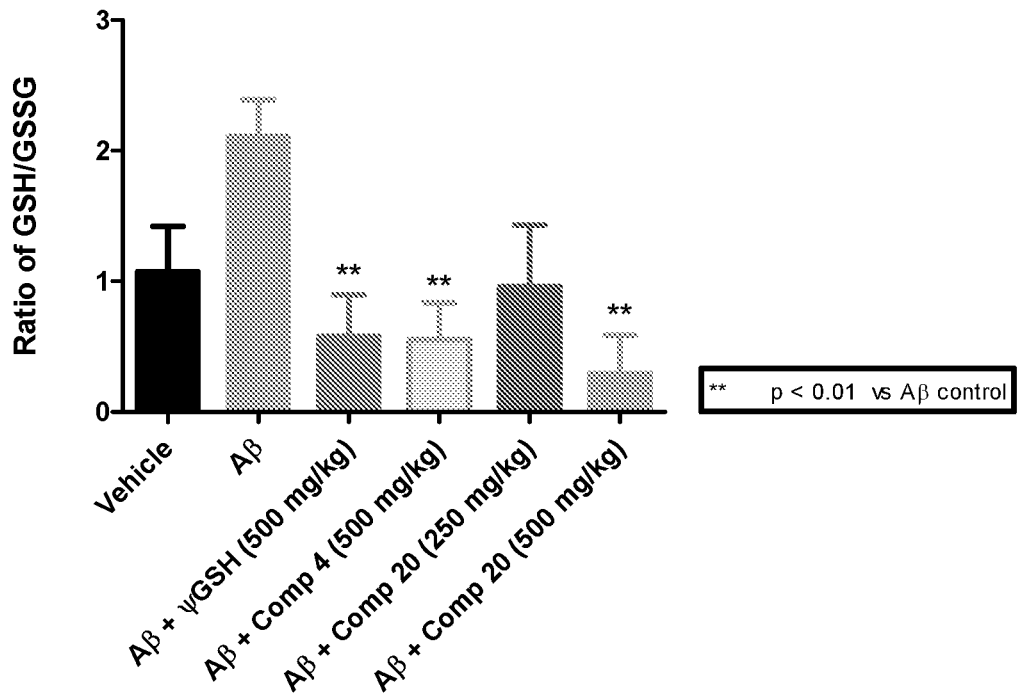
Figure 14:
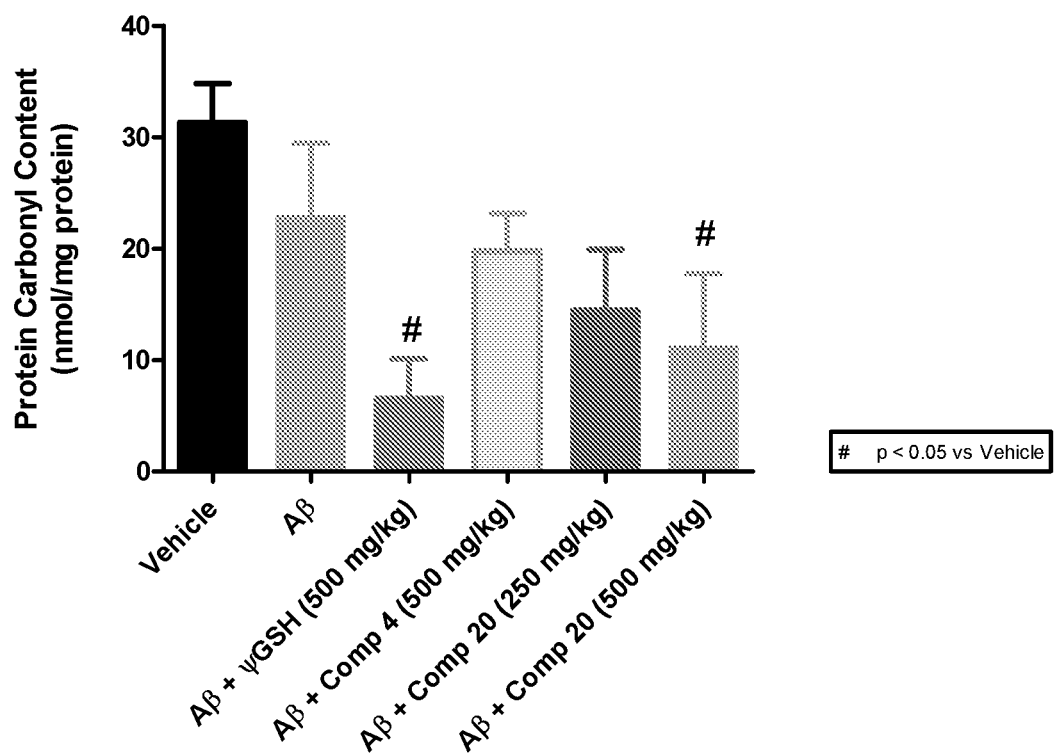
FIG. 14 Quantitation of protein carbonyl content in the hippocampus of mice treated with compounds.
Figure 15:
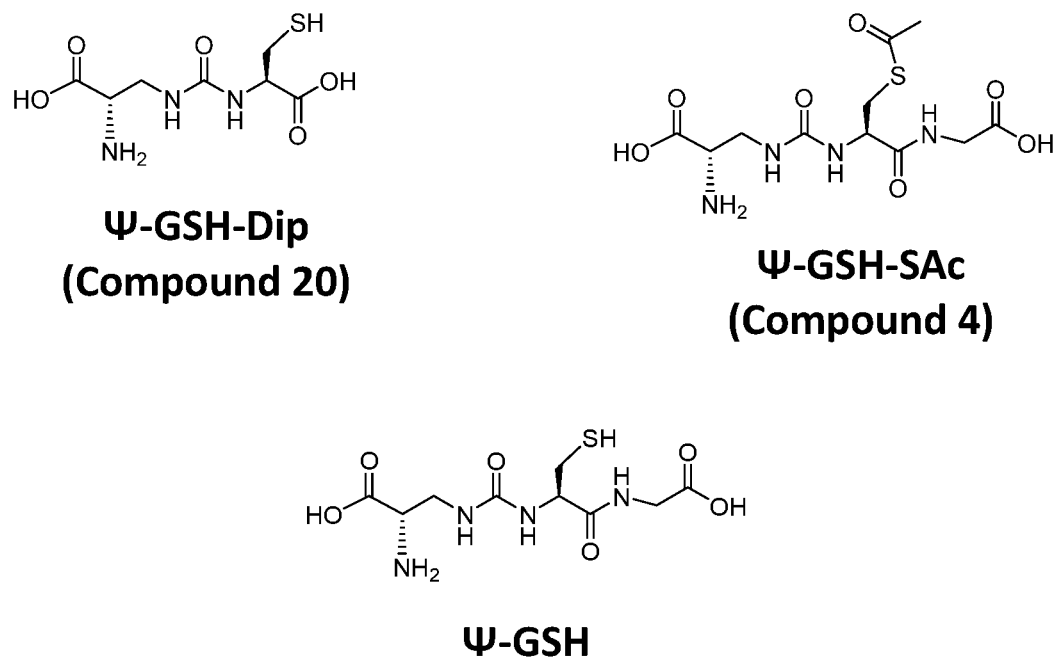
FIG. 15 shows structures of compounds 4, 20 and ψ-GSH.

Spontaneous alternation in a T-maze was used to assess working memory abilities, based on the innate tendency of mice to alternate their choice of a goal arm based on their recall of the initial choice. The T-maze used was made of black Plexiglas as per dimensions stated in Nat Protocols, 2006, 7-12. Mice were placed in the start arm with the central divider in place so that when entering either of the goal arms the mice were not able to see the other one. After being confined to the start arm for 60 seconds, the animal was allowed to move freely for a total of 15 arm entrees. Mice that did not complete the task or took more than 30 min to complete the task were excluded. The alternation percentage was calculated by dividing the number of times the animal entered alternating arms by 14 (free-choice trials). An arm entry is defined as the animal's tail tip entering the arm and repetitive arm entries as an animal re-entering the same arm three times in a row (e.g., 5 sequential entries into the same arm is 3 repetitive entries). Ratio of right and left arm entries was calculated to determine spatial preference of mice in different treatment groups. The data were analyzed using repeated measures analysis of variance (ANOVA) using Dunnett test. FIG. 3 shows a timeline for the experimental protocol FIGS. 4 and 5 show the results of these studies. No apparent toxicity was observed in groups treated with the compounds at the doses tested (determined by body weight changes and mice behavior). All of the compounds tested restored working memory in mice injected with i.c.v. Aβ peptide. The efficacy of compounds was comparable in this cognitive test as determined by complete restoration of alternation behavior and less repetitive entries when compared to Aβ only group.

Biochemical Analysis

After behavioral tests, the mice were sacrificed, and the brain was immediately removed. Half of brain tissue were fixed in 4% paraformaldehyde solution for histopathology, the other half was stored at −80° C. for the biochemical studies.

The brain tissue for biochemical analysis was rapidly homogenized in these buffers 1) TBS (20 mM Tris-HCl and 150 mM NaCl) buffer with protease inhibitors and 5 M Guanidine-HCl in 50 mM Tris-HCl buffer for Aβ1-42 ELISA assay, 2) 50 mM MES buffer for GSH and Protein Carbonyl assay, 3) RIPA buffer with protease inhibitors for TBARS assay. Then the homogenates were centrifuged at 10,000 g at 4° C. for 20 min. The supernatant was collected and was used to measure according to the manufacturer's directions.

$A\beta^{1-42}$ ELISA assay.

The $A\beta^{1-42}$ in the brain was measured using a sensitive and specific ELISA assay according to the manufacturer's instructions (Immuno-Biological Laboratories Co., Ltd., Japan). A total of 100 μl of sample was added to each well, and then the plate was incubated overnight at 4° C. After several washes, 100 μl of labeled antibody was added to each well, and the plate was incubated at 4° C. for 1 hour. After several washes, the chromogen (100 μl) was added, followed by incubation for 30 min at room temperature in the dark. The reaction was stopped after adding stop solution (100 μl); the absorbance at 450 nm was detected on a Spectra Max M5 microplate reader. A standard curve with known amounts of $A\beta^{1-42}$ was also generated. The $A\beta^{1-42}$ level was calculated according to the standard curve.

Glutathione (GSH) and GSSG level.

The brain GSH and GSSG level were measured with Glutathione assay kit (Cayman Chemical, Ann Arbor, Mich.). A total of 50 μl of sample was added to each well, and 150 μl the assay cocktail (MES buffer, reconstituted cofactor mixture, enzyme mixture, water, and DTNB) was added to the wells. The absorbance was measured at 414 nm using Spectra Max M5 microplate reader. Assay range was calculated under the standard curve (0-16 μM GSH or 0-8 μM GSSG). Results were expressed as nmol/mg protein and ratio of GSH/GSSG.

Protein Carbonyl Assay

The protein carbonyl content is used as a marker of protein oxidation. The amount of protein-hydrozone produced is quantified spectrophotometrically by Protein Carbonyl Colorimetric assay kit (Cayman Chemical, Ann Arbor, Mich.). 100 μl of sample was transferred into two tubes, one containing 400 μl of DNPH and the other tube containing 400 μl of 2.5 M HCl. Both tubes were incubated in the dark at room temperature for one hour. After incubation, 500 μl of 20% TCA was added to each tube, placed the tubes on ice and incubated for five minutes. The tubes were centrifuged at 10,000 g for 10 min at 4° C., the pellet was resuspended in 500 μl of 20% TCA, and centrifuged the tubes at 10,000 g for 10 min at 4° C. The pellet obtained was resuspended in 500 μl of (1:1) ethanol/ethyl Acetate mixture and centrifuged at 10,000 g for 10 min at 4° C. This step was repeated two more times. After the final wash, the protein pellets were resuspended in 500 μl of guanidine hydrochloride with vortex, centrifuged at 10,000 g for 10 min at 4° C., and then transferred to a 96-well plate. The absorbance was measured at 385 nm using Spectra Max M5 microplate reader.

Histopathological Examination.

For histopathology, the brain tissues were fixed in 4% paraformaldehyde (PFA) solution for 72 h, then transferred to 20% sucrose for at least 16 h until they sank for cryoprotection. The brain tissues were then kept in the final 30% sucrose solution until sectioning. Serial (neighboring) sections of 8 μm thickness were cut and stained with GFAP antibody with IHC (frozen section) protocol. The sections were dried at room temperature for 30 min, and fixation in acetone:methanol (1:1) at −20° C. for 10 min. After fixation, the sections were boiled in 10 mM citrate buffer, 0.05% Tween 20, pH 6.0 for antigen retrieval with microwave for 5 min and cooled to room temperature. The sections were washed with PBST, and blocked in 5% normal goat serum for 30 min in humid chamber. The sections were stained with GFAP (1:1000 dilution in PBS with 1% BSA) overnight at 4° C. After washing off primary antibody, mouse anti-rabbit IgG HRP conjugated secondary antibody (1:2000 dilution in PBST) was applied for one hour and DAB kits according to the manufacturer's protocols. All stained sections were photographed at ×200 magnifications and counted using an imaging software.

Example 2

The following illustrate representative pharmaceutical dosage forms, containing a compound of formula I ('Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X= (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X= (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A compound of formula I:

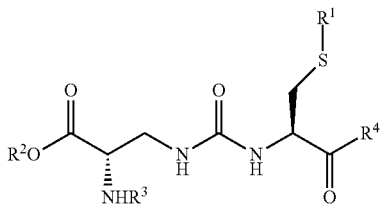

I wherein:
R$^1$ is —C(=O)—R$^{1a}$ or —C(=O)O—R$^{1b}$;
R$^{1a}$ is (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{1a}$ is optionally substituted with 1-5 halo, (C$_1$-C$_3$)alkyl, —OH, —SH, or —NHC(=O)(C$_1$-C$_3$)alkyl;
R$^{1b}$ is (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{1b}$ is optionally substituted with 1-5 halo, (C$_1$-C$_3$)alkyl, —OH, —SH, or —NHC(=O)(C$_1$-C$_3$)alkyl;
each R$^2$ is independently H, (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^2$ is optionally substituted with 1-5 halogen or (C$_1$-C$_3$)alkyl;
R$^3$ is H, —C(=O)—R$^{3b}$ or —C(=O)O—R$^{3b}$;
R$^4$ is

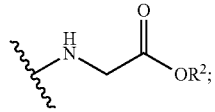

each R$^{3b}$ is independently (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{3b}$ is optionally substituted with 1-5 halo, (C$_1$-C$_3$)alkyl, —OH, —SH, or —NHC(=O)(C$_1$-C$_3$)alkyl;
or a salt thereof.

2. The compound of claim 1 wherein the compound of formula I is a compound of formula Ia:

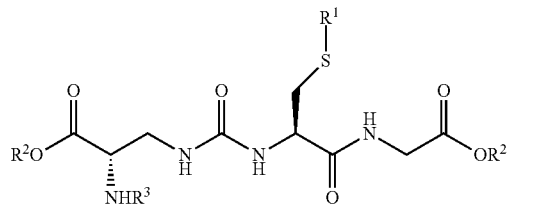

Ia wherein:
R$^1$ is —C(=O)—R$^{1a}$ or —C(=O)O—R$^{1b}$;
R$^{1a}$ is (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{1a}$ is optionally substituted with 1-5halo, (C$_1$-C$_3$)alkyl, —OH, —SH, or —NHC(=O)(C$_1$-C$_3$)alkyl;
R$^{1b}$ is (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{1b}$ is optionally substituted with 1-5halo, (C$_1$-C$_3$)alkyl, —OH, —SH, or —NHC(=O)(C$_1$-C$_3$) alkyl;
each R$^2$ is independently H, (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^2$ is optionally substituted with 1-5halogen or (C$_1$-C$_3$)alkyl;
R$^3$ is H, —C(=O)—R$^{3b}$ or —C(=O)O—R$^{3b}$;
each R$^{3b}$ is independently (C$_1$-C$_6$)alkyl, (C$_2$-C$_6$)alkenyl, (C$_3$-C$_8$)cycloalkyl, 6-10 membered aryl, or 5-10 membered heteroaryl, wherein any (C$_1$-C$_6$)alkyl, (C$_2$-C$_6$)alkenyl, (C$_3$-C$_8$)cycloalkyl, 6-10 membered aryl, or 5-10 membered heteroaryl of R$^{3b}$ is optionally substituted with 1-5 halo, (C$_1$-C$_3$)alkyl, —OH, —SH, or —NHC(=O)(C$_1$-C$_3$)alkyl;
or a salt thereof.

3. The compound or salt of claim 1, wherein R$^{1a}$ and R$^{1b}$ are independently methyl, ethyl, or butyl.

4. The compound or salt of claim 1, wherein $R^1$ is —C(=O)CH$_3$, —C(=O)(CH$_2$)$_3$CH$_3$, or —C(=O)OCH$_2$CH$_3$.

5. The compound of claim 1 that is:

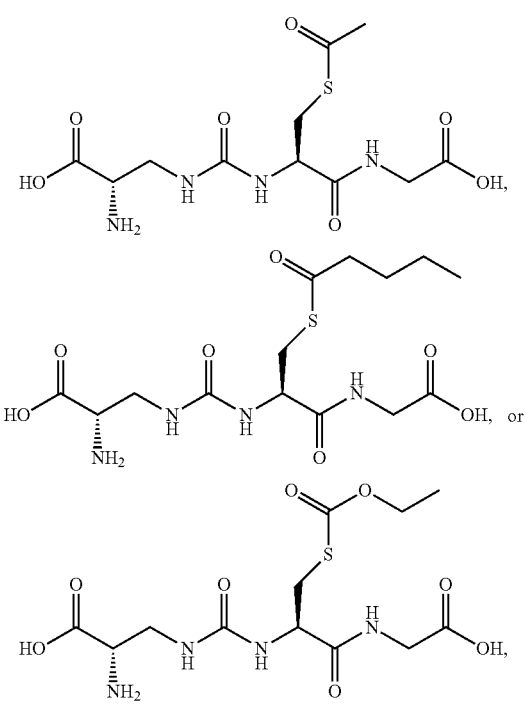

or a salt thereof.

6. The salt of claim 1, wherein the salt comprises DMAE.

7. A salt of claim 1 that is a DMAE salt of:

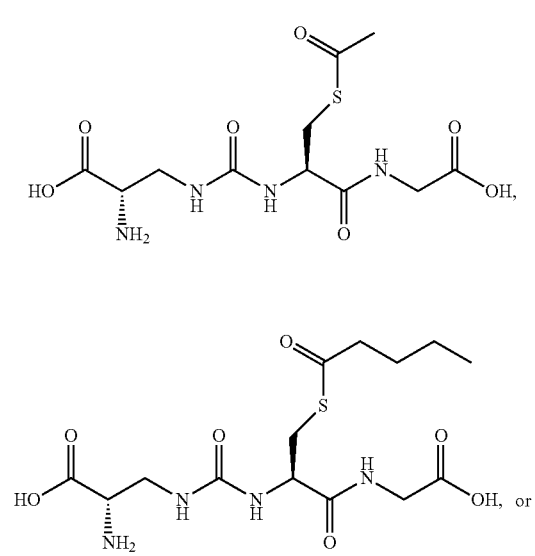

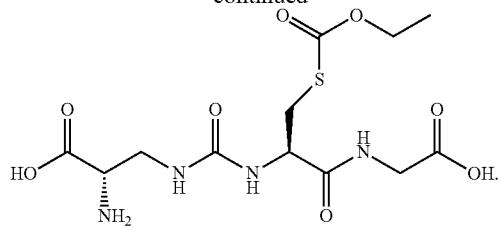

8. The salt of claim 7, wherein the salt comprises about 1.8 to about 2.2 molecules of DMAE and one molecule of the compound of formula I.

9. The salt of claim 1 that is:

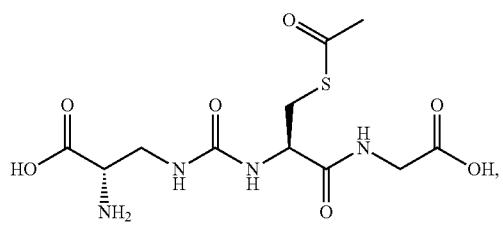

2 DMAE

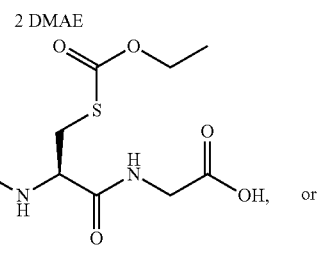

2 DMAE

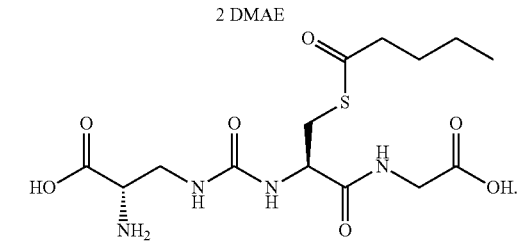

2 DMAE

10. The salt of claim 1, wherein the compound of formula I is in the form of a DMAE (dimethylaminoethanol) salt.

11. The salt of claim 1, wherein the salt comprises about 1.8 to about 2.2 molecules of DMAE and one molecule of the compound of formula I.

12. A pharmaceutical composition comprising a compound as described in claim 1 or a pharmaceutically acceptable salt thereof, and a pharmaceutically acceptable diluent or carrier.

13. A method for treating Alzheimer's Disease, Parkinson's Disease, or amyotrophic lateral sclerosis (ALS) in a mammal, comprising administering a compound as described in claim 1 or a pharmaceutically acceptable salt thereof, to the mammal.

* * * * *